United States Patent
Hudson et al.

(10) Patent No.: US 8,700,424 B2
(45) Date of Patent: Apr. 15, 2014

(54) PLATFORM FOR CONNECTING MEDICAL INFORMATION TO SERVICES FOR MEDICAL CARE

(75) Inventors: Peter Hudson, Evergreen, CO (US); Wayne Guerra, Bow Mar, CO (US)

(73) Assignee: iTriage, LLC, Denver, CO (US)

( * ) Notice: Subject to any disclaimer, the term of this patent is extended or adjusted under 35 U.S.C. 154(b) by 343 days.

(21) Appl. No.: 12/630,696

(22) Filed: Dec. 3, 2009

(65) Prior Publication Data

US 2010/0145723 A1    Jun. 10, 2010

Related U.S. Application Data

(60) Provisional application No. 61/200,762, filed on Dec. 3, 2008, provisional application No. 61/200,763, filed on Dec. 3, 2008.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | | |
|---|---|---|---|
| 5,594,638 A | 1/1997 | Iliff | |
| 5,660,176 A | 8/1997 | Iliff | |
| 5,711,297 A | 1/1998 | Iliff | |
| 5,724,968 A | 3/1998 | Iliff | |
| 5,868,669 A | 2/1999 | Iliff | |
| 5,910,107 A | 6/1999 | Iliff | |
| 5,935,060 A | 8/1999 | Iliff | |
| 6,022,315 A | 2/2000 | Iliff | |
| 6,071,236 A | 6/2000 | Iliff | |
| 6,113,540 A | 9/2000 | Iliff | |
| 6,234,964 B1 | 5/2001 | Iliff | |
| 6,270,456 B1 | 8/2001 | Iliff | |
| 6,468,210 B1 | 10/2002 | Iliff | |
| 6,475,143 B2 | 11/2002 | Iliff | |
| 6,482,156 B2 | 11/2002 | Iliff | |
| 6,524,241 B2 | 2/2003 | Iliff | |
| 6,527,713 B2 | 3/2003 | Iliff | |
| 6,569,093 B2 | 5/2003 | Iliff | |
| 6,641,532 B2 | 11/2003 | Iliff | |
| 6,725,209 B1 | 4/2004 | Iliff | |
| 6,730,027 B2 | 5/2004 | Iliff | |
| 6,746,399 B2 | 6/2004 | Iliff | |
| 6,748,353 B1 | 6/2004 | Iliff | |
| 6,764,447 B2 | 7/2004 | Iliff | |
| 6,767,325 B2 | 7/2004 | Iliff | |
| 6,770,029 B2 | 8/2004 | Iliff | |

(Continued)

FOREIGN PATENT DOCUMENTS

JP    2005135051    5/2005

*Primary Examiner* — Dilek B Cobanoglu
*Assistant Examiner* — Robert Sorey
(74) *Attorney, Agent, or Firm* — Marsh Fischmann & Breyfogle LLP

(57) ABSTRACT

A user device for connecting symptom, disease, procedure, and facility based information into actionable services for medical care and cost analysis is presented. The user device may include the functionality of linking medical information and providing user specific information. The user-specific information allows the user to make an informed decision about medical treatment. The user device may further be operative to tailor information in light of user characteristics such as location or healthcare network membership.

49 Claims, 28 Drawing Sheets

(56) References Cited

U.S. PATENT DOCUMENTS

| | | |
|---|---|---|
| 6,817,980 B2 | 11/2004 | Iliff |
| 6,849,045 B2 | 2/2005 | Iliff |
| 7,297,108 B2 | 11/2007 | Iliff |
| 7,297,111 B2 | 11/2007 | Iliff |
| 7,300,402 B2 | 11/2007 | Iliff |
| 7,306,560 B2 | 12/2007 | Iliff |
| 7,912,736 B2 * | 3/2011 | Wyatt ................................ 705/3 |
| 8,010,386 B2 * | 8/2011 | Wyatt ................................ 705/4 |
| 2003/0167187 A1 * | 9/2003 | Bua .................................... 705/2 |
| 2004/0073455 A1 | 4/2004 | McConnochie et al. |
| 2004/0078220 A1 | 4/2004 | Jackson |
| 2004/0128168 A1 * | 7/2004 | Wyatt ................................ 705/2 |
| 2005/0039127 A1 | 2/2005 | Davis |
| 2005/0240443 A1 * | 10/2005 | Salman et al. .................... 705/3 |
| 2005/0283385 A1 | 12/2005 | Hunkeler et al. |
| 2006/0015369 A1 | 1/2006 | Bachus et al. |
| 2006/0053035 A1 * | 3/2006 | Eisenberg ........................ 705/2 |
| 2006/0100904 A1 | 5/2006 | Jee et al. |
| 2008/0059227 A1 | 3/2008 | Clapp |
| 2008/0300918 A1 * | 12/2008 | Tenenbaum et al. ............. 705/2 |
| 2009/0089085 A1 * | 4/2009 | Schoenberg .................... 705/2 |
| 2009/0259488 A1 * | 10/2009 | Gounares et al. ................ 705/3 |
| 2010/0017222 A1 * | 1/2010 | Yeluri et al. ..................... 705/2 |
| 2010/0070295 A1 * | 3/2010 | Kharraz Tavakol et al. ...... 705/2 |

* cited by examiner

PLATFORM FOR CONNECTING MEDICAL INFORMATION TO SERVICES FOR MEDICAL CARE

RELATED APPLICATIONS

This application claims priority to U.S. Provisional Application Ser. No. 61/200,762 filed Dec. 3, 2008, entitled "MOBILE PHONE PLATFORM FOR CONNECTING PROBLEMS, CAUSATIVE CONDITIONS, AND FACILITY BASED INFORMATION FOR COMPLEX SYSTEMS INTO ACTIONABLE SERVICES FOR SERVICE PROVISION AND COST ANALYSIS," the entirety of which is hereby incorporated by reference, and U.S. Provisional Application Ser. No. 61/200,763, filed Dec. 3, 2008, entitled "MOBILE PHONE PLATFORM FOR CONNECTING SYMPTOM, DISEASE, PROCEDURE, AND FACILITY BASED INFORMATION INTO ACTIONABLE SERVICES FOR MEDICAL CARE AND COST ANALYSIS," the entirety of which is hereby incorporated by reference.

FIELD OF THE INVENTION

The present invention relates generally to a system and associated functionality for identifying facilities and service providers, as well as providing other information, based on user inputs concerning symptoms or conditions. The invention is particularly useful for providing information about medical providers based on inputs concerning symptoms, e.g., via a mobile platform such as a cell phone or PDA.

BACKGROUND OF THE INVENTION

In a variety of contexts, it is difficult for a layperson or other user to obtain actionable information regarding needed products or services because of various barriers between the user's indication of what the user needs and existing data concerning available products or services. The case of a layperson or other user desiring information regarding medical services is illustrative. Many sources of information are available to identify medical facilities and service providers based on specialty. Such sources of information include telephone books and web-based resources. Unfortunately, while a layperson or other user typically knows what symptoms are being presented or, in some cases, what type of medical consultation is desired (e.g., a check-up or a colonoscopy), in many cases the user will not necessarily know what specialty is needed. That is, a layperson with particular symptoms may not be able to determine that those symptoms indicate a particular condition requiring the service of a particular type of specialist, for instance, a gastroenterologist.

Even if the user could somehow identify the correct specialty to address the user's need, a number of obstacles may remain. For example, the user may be faced with the complication of identifying an "in network" service provider for his health plan, and/or identifying an appropriate service provider or facility close to the user's location (which may be particularly problematic when the user is traveling or is otherwise unfamiliar with the area). In view of all of these obstacles, the user may have difficulty in timely obtaining actionable information regarding medical services, e.g., what facility/type of specialist is needed, which appropriate specialists are in-network, which of those in-network specialists are nearby, where are the medical providers and what are the directions to get there, what other information is available to describe the user's condition, is the specialist/provider available and what are the wait times or other latency periods, is there anything the user needs to know or do until professional treatment is available, etc. It will be appreciated that the inability to timely obtain such information can be annoying in the best of circumstances but hazardous in some cases.

The ability to quickly and easily obtain information regarding medical care services would benefit not only lay people but also skilled service providers such as physicians, nurses and EMTs. For example, an EMT professional (and those under the EMT's care) may benefit from access to substantially real-time information identifying nearby facilities/physicians available to treat patients as well as wait times, traffic delays, preferred driving directions, etc. Nurses and physicians may be happy to have assistance in confirming diagnoses and identifying appropriate specialists for referrals. While various diagnostic tools and service resources are available, the existing tools and resources often do not effectively provide the needed specific information based on the types of user inputs that are available as a practical matter.

SUMMARY OF THE INVENTION

The present invention is directed to providing user-specific, actionable information that meaningfully connects the user seeking information to the information sought such that the user may make informed decisions regarding the topic upon which information is sought and in turn act on the information provided. In this regard, in accordance with the present invention, not only is the user provided access to available information on a topic, but also is provided actionable information in the form of information specific to the user.

A particularly useful application of the present invention is in the medical field. Despite the existence of a vast amount of medical information, particularly on the Internet, there still exists a need for a system that provides information based on specific user needs and that allows a user to take action based on that information.

Therefore, the present invention provides a method and apparatus for providing access to actionable medical information. In addition to the ability to navigate the information provided, the invention provides specific information that enables the user to resolve a unique need that the user may have. For instance, the invention may allow a user to input information regarding (i) a symptom; (ii) a disease or condition; (iii) a procedure; or (iv) a medical facility or provider, and receive actionable information regarding that user's needs as determined based on the user input. As such, the invention enables the user make a personalized decision regarding actions to address the needs of the user.

This actionable information may be associated with functionality of a computer-based processing system (a user device, remote network server and/or other platform) that allows the user to take action to address a medical event in the most appropriate manner. This functionality may include providing connectivity to act on the actionable information by way of a telephone network, a data network, e-mail, instant messaging or the like. The functionality may also include determining a location of the user to provide user specific information corresponding to local or nearby facilities or medical providers. For instance, the actionable information may be useful for calling a medical provider, calling a nurse line, performing a structured web search, accessing video content, mapping facilities, or calling facilities directly.

Moreover, the invention enables tailoring the actionable information provided to the user based on one or more of the user, a network accessed by the user, and/or a characteristic of either or both the user and/or the network. For instance, as stated above, the invention may involve determining a location of a user. Thus, the information provided may correspond to the location of a user. Furthermore, other information may be used to tailor the information to individual users. By way of example, a user may be able to indicate to a user device, or an associated system may be otherwise able to obtain, information relating to a healthcare network (e.g., an insurance provider) to which the user belongs. Furthermore, the invention may be capable of presenting information regarding a medical specialist in response to inputs by the user. Additional functionality to assist medical professionals may be facilitated as well. For instance, medical professionals may use the invention to verify or assist in determining a diagnosis or may use the invention to assist in providing recommendations and referrals to patients. Furthermore, real-time information regarding facilities may be provided by the invention to assist in making medical decisions by medical professionals. For instance, the invention may provide estimates regarding latency to doctor consultation times. Such information may be compiled using a variety of parameters, including traffic, facility loads, doctor staffing, or other factors that determine patient wait times. As such, patients may be directed to facilities such that the latency to doctor consultation time is diminished.

In this regard, in accordance with one aspect of the present invention, a method and apparatus ("utility") is provided for identifying an in-network medical provider or health professional based on symptoms. The utility involves receiving, at a computer-based processing system (e.g., a local user device or remote server), information regarding a symptom from a user. For example, the user may enter a textual description of a symptom or select a symptom from a menu of pre-defined symptoms. The utility further involves correlating, using the processing system, the symptom to conditions that present the symptom and obtaining healthcare network information regarding a healthcare network to which the user belongs. For example, the user may provide healthcare network information directly to the processing system, the system may be able to determine a healthcare network for a user based on the user accessing a network, or the system may be operative to infer an association with a healthcare network based on some other user information (e.g., the user's employer, military status, location, etc.). The utility also involves identifying a medical provider, using the processing system based on the condition and the healthcare network information and presenting information regarding a medical provider to the user.

In accordance with another aspect of the present invention, a utility is provided for identifying a medical provider or health professional based on symptoms and a location of the user. The utility involves receiving, at a computer-based processing system, information regarding a symptom from a user and correlating the symptom to a condition. The utility further involves acquiring information regarding a location of the user. For example, the processing system may acquire the location of the user from the user (or a user device) or it may determine the location of the user by another method e.g., a cell identification (for a network cell, cell sector or microcell), time difference of arrival, angle of arrival, etc. The utility may involve identifying, using the processing system, a medical provider based on at least the condition and the location of the user and presenting information regarding the medical provider to the user.

In accordance with another aspect of the present invention, a user device is provided for obtaining medical information. The user device includes input structure for receiving healthcare network information regarding a healthcare network to which a user belongs and symptom information regarding a symptom of the user. The user device also includes a network interface for transmitting patient information based at least in part on the healthcare network information and the symptom information to a network platform and receiving responsive medical provider information from the platform. The user device also includes output structure for providing the medical provider information to the user.

In accordance with another aspect of the present invention, a computer-based processing system for providing medical information is provided. The system includes input structure for receiving information regarding a symptom from a user. The system further includes a processor in operative communication with at least one database containing information regarding a condition. The processor is operative to obtain healthcare network information regarding a healthcare network to which the user belongs. For example, the processor may receive healthcare network information from the user or may obtain such information indirectly (e.g., by way of a network accessed by the user or information regarding a user not directly indicative of a healthcare network). The processor is also operative to access the database and correlate the information regarding a symptom and a condition and to identify a medical provider based on the condition and the healthcare network information. The system also includes output structure for providing information regarding the medical provider to the user. The computer-based processing system can be locally resident on a user device, remotely resident on one or more network platforms, or distributed over the local device and remote platform(s).

BRIEF DESCRIPTION OF THE DRAWINGS

For a more complete understanding of the present invention and further advantages thereof, reference is now made to the following detailed description taken in conjunction with the drawings in which.

DETAILED DESCRIPTION OF THE DRAWINGS

Reference will now be made to the accompanying drawings, which at least will assist in illustrating the various pertinent features of the present invention. In this regard, the following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to enable others skilled in the art to utilize the invention as described or in other embodiments and with various modifications required by the particular applications or uses of the present invention.

Figure 1:
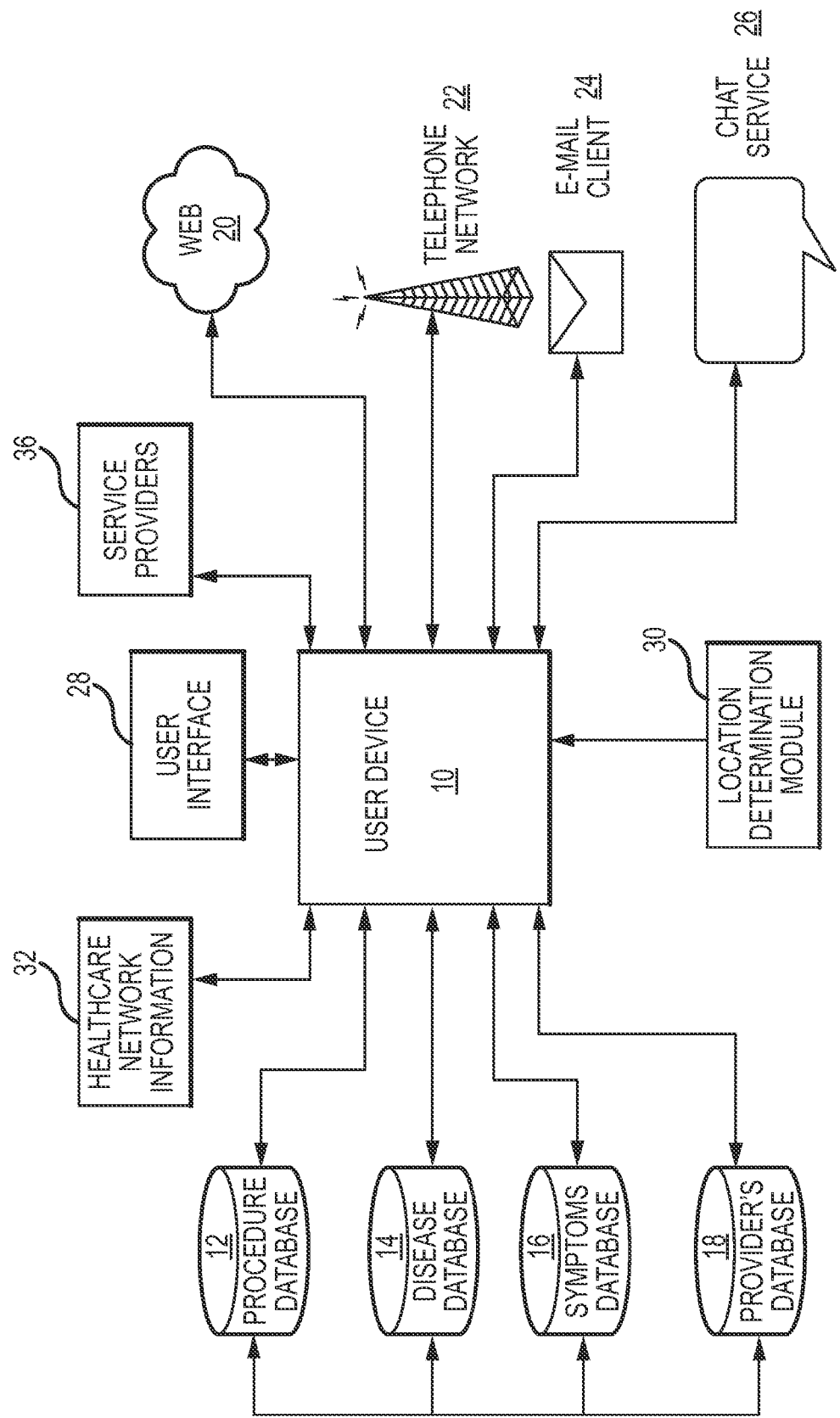
FIG. 1 is a schematic view of an embodiment of a user device in accordance with the present invention.

FIG. 1 is a schematic view showing a user device 10 in accordance with the present invention. The user device 10 may generally be a computer-based processing system. The user device 10 may be executed using, among other components, a microprocessor, memory, a data bus, I/O components, and the like. The user device 10 may further be embodied in a variety of systems and devices. Examples of such systems and devices include desktop computers, laptop computer, mobile phones, PDAs, other handheld devices, or the like. The functionality described below may be executed locally on the user device 10, remotely on one or more network platforms or distributed between the user device 10 and remote network platform(s). For example, at least some of this functionality may be implemented by an application running locally on the device 10. Alternatively or additionally, at least some logic may be web-based such that at least some of the functionality is executed as a web application in a browser using scripts or other language (e.g., HTML, Java, Script, etc.). Additionally, the user device 10 may be embodied as a mobile device, such as a mobile phone, other handheld PDA device, or the like. When the user device 10 is embodied in a mobile device, the functionality may be executed from the mobile device and reside in memory thereof or may be executed as a web application as described above.

The user device 10 may be functional to access a number of data repositories herein termed databases. These databases, for instance, may include a procedure database 12, a disease/condition database 14, a symptoms database 16, and a provider database 18. Other databases could be provided consistent with the description provided below. By way of example, the procedure database 12 may include information regarding medical procedures. This information may include steps of each procedure, the type of medical specialist capable of performing the procedure, possible complications of the procedure, average cost of the procedure, or other information regarding the procedure.

The user device 10 may also access a disease database 14. The disease database 14 may contain information regarding diseases or medical conditions. The database 14 may include information about the disease or medical condition, such as the description of the disease, tests that may be run to determine or diagnose the disease, common symptoms of the disease and common treatments of the disease.

The user device may also access a symptoms database 16. The symptoms database 16 may include information regarding possible symptoms suffered by individuals as a result of a medical conditions or diseases. The symptom database 16 may include information regarding conditions or diseases that present the symptoms contained in the symptom database 16. The symptom database 16 may further include information regarding symptoms (e.g., drugs or techniques used to alleviate symptoms, etc.).

Additionally, the user device 10 may access a provider database 18. The provider database 18 may include information about a number of medical providers including, but not limited to, emergency rooms, urgent care clinics, retail clinics, specialists, physicians, pharmacies, or other medical providers. Moreover, the provider database 18 may include information regarding each medical provider such as insurance network information, information regarding facilities (e.g. hours of operation, location, staffing information, real-time wait times, etc. or other information), as well as reviews or user comments about each medical provider.

For any database accessible by the user device 10, in one embodiment, the database(s) may be resident on the device upon which the associated functionality is executed. In this regard, the databases may be stored locally in memory accessible by a processor of the user device 10 to execute the functionality in accordance with the description provided below. Alternatively, in another embodiment, the databases may be stored at a remote location that may be accessed by the user device 10 via a network or other means. For example, the databases may be stored on a remote server accessible by the user device by utilizing the Internet or other wide area network. As a further alternative, the databases, or any one thereof, may be distributed as between the user device 10 and one or more remote network servers.

Additionally, the user device 10 may be in operative communication with one or more communication networks. These communication networks may include, by way of example a data network 20, a telephone network 22, an e-mail client 24, a chat service 26, other communication networks, or a combination of the foregoing. For instance, the user device 10 may include the ability to connect to the internet, access e-mail clients, or utilize chat services. If the user device 10 is embodied as a mobile device such as mobile phone, the user device 10 may utilize integrated functionality of the mobile device to connect to the networks.

The illustrated user device 10 may include input structure. Furthermore, the user device 10 may include output structure. In one embodiment of the user device 10, the input structure and output structure may be integrated into a user interface 28. The user interface 28 may allow users to interact with the user device 10. The user interface 28 may include any known means of interaction with an electronic device such as for example, a keyboard, mouse, touch screen display, voice command, or any other known means in the art. Additionally, the user interface 28 may include a display or other device capable of displaying information to a user. Other input structure may be provided, for example, a communication gateway for receiving data. For instance, the input structure could be an input port of a network server or the like that facilitates receipt of data (e.g., using an communication protocol such as http, ftp, TCP/IP, etc.). Similarly, the output structure could comprise an output port of network server or the like that facilitates transmission of data.

The user device 10 may also utilize a location determination module 30 in order to determine and/or relay the location of a user. The location services 30 may be provided using several techniques known in the art. For instance, the location services 30 may utilize existing information stored in memory in order to determine the location of the user. In this regard, the user may have a profile stored in the on their computer containing information such as the user's home address, work address, or general geographic location. This information may be accessed by the user device 10 to ascertain information about the location of a user. Alternatively, the location services 30 may utilize integrated functionality of the user device 10 (e.g., the user device 10 may include location resolving devices). For example, the device may be equipped with a GPS receiver capable of determining the location of a user using the device or logic for determining the location of the device based on network structures (e.g., handset-based cell location, cell sector, microcell, angle of arrival, time difference of arrival, signal strength, etc.). The user device 10 in turn may utilize this location information. Other methods of providing a user location may include network-based location determination technologies and accessing location information from a location gateway of a wireless network. Accordingly, the location information may be obtained from the user device 10 or another source.

The user device 10 may also be operative to receive personalized medical information or may employ other means of determining personalized medical information for the user. The personalized medical information may comprise healthcare network information 32 and may include information regarding a user's insurance policy or other healthcare network to which the user belongs. The user device 10 may obtain the healthcare network information 32 in a variety of manners. For instance, the user may simply input healthcare network information 32. Alternatively, the user device 10 may determine healthcare network information 32 for the user based on a network accessed by the user (e.g., if the user accesses an insurance provider's website or otherwise logs into a healthcare network provider's network). Alternatively, the user device 10 may obtain the healthcare network information 32 by inferring a healthcare network to which the user belongs based on information provided by the user not directly related to healthcare network information (e.g., the user's employer, military status, age, etc.) Furthermore, the healthcare network information 32 may include a patient history or family medical history. User device 10 may be operative to send to or to receive personalized medical information regarding a user's condition, diseases, medical history or other information about the user.

Additionally, the user device 10 may be in communication with a number of service providers 36. These may include many different kinds of healthcare or other types of service providers. For instance, the service providers 36 may provide advertisement information or other information (medical and otherwise) to users by way of the user device 10 for use by the user. Alternatively, the user device may access the service provider's content and use the content in the execution of user device 10.

Figure 2:
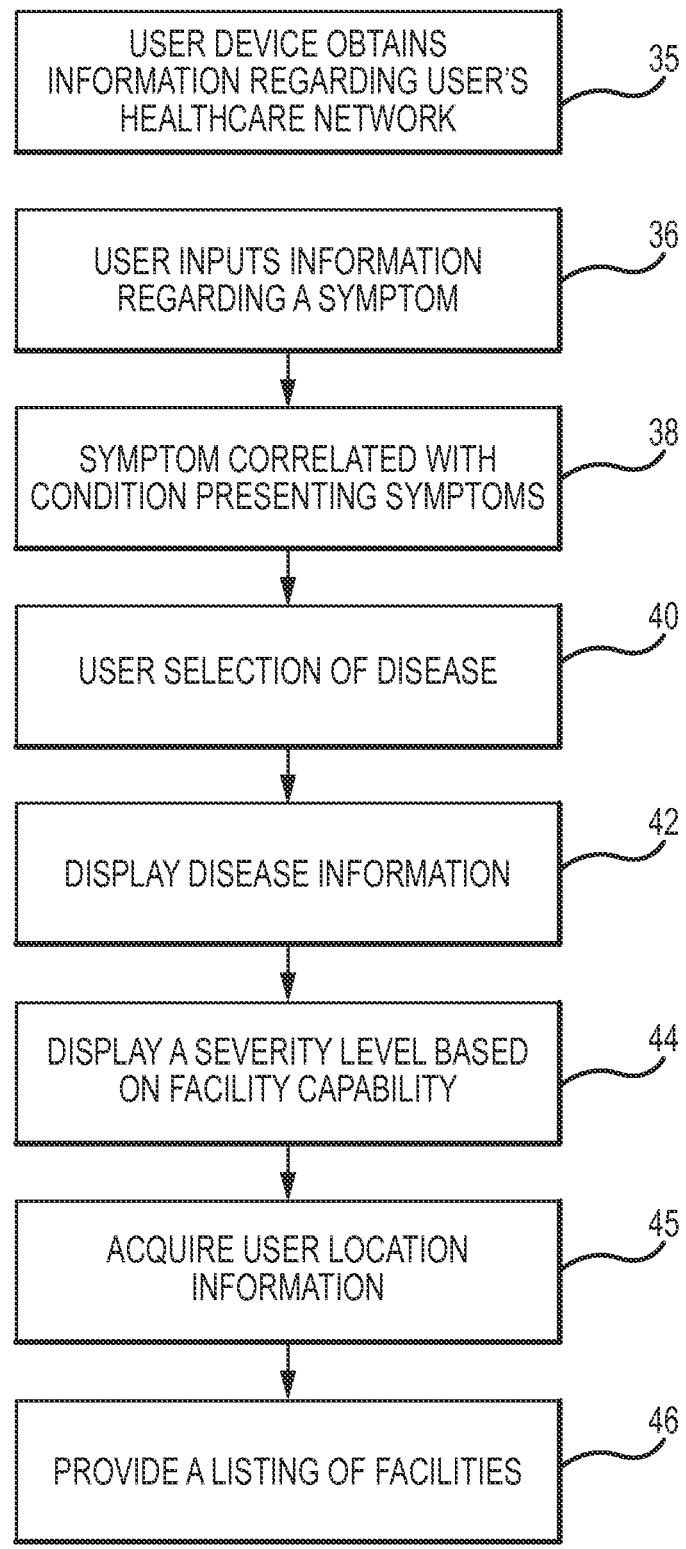
FIG. 2 is a flowchart depicting a method in accordance with the present invention.

Turning to FIG. 2, a flow chart is provided that depicts certain functionality of the user device 10 and/or other platform. The user device may obtain (35) information regarding a user's healthcare network as was described above. In FIG. 2, the user inputs (36) a symptom or chooses a symptom from a list that may be contained in the symptom database 16. The user device 10 then correlates (38) the selected symptom to medical conditions or diseases characterized as commonly associated with the selected symptom. Also, the conditions or diseases commonly associated with the presenting symptom may be displayed to the user by way of the user interface 28. The user can then select (40) a disease or condition of interest from the list correlated (38) conditions or disease. In this regard, the user device may display (42) information about the selected disease or condition including all information associated with the disease as is contained in the disease database 14. This information is displayed to the user such that the user may choose to further explore the information regarding the disease. That is, the disease information may be displayed at various levels allowing the user to explore the information about the disease from various levels of specificity.

The user may be presented (44) with and may select from a provider list of capable providers that can treat or provide therapy for the disease or condition selected. This may include displaying a plurality of types of providers stratified by the severity level of either the condition or symptom. In return, facilities that have the capabilities to address the symptom or disease selected may be presented to the user. For instance, if the disease selected is life threatening or of an emergency nature, the display may show that the facilities capable of providing treatment are limited to emergency rooms. Alternatively, less severe or serious diseases or conditions selected may be correlated to other facilities such as physicians, pharmacies, urgent care facilities or other medical providers based on the severity of the disease selected.

The user device may acquire (45) user location information. Again, the user device may use a location determination module 30 as described above to acquire (45) information that allows the user device to determine a location of the user. Furthermore, the user device may provide (46) a location based listing of the facilities corresponding to the facilities displayed. Again, this may utilize the location determination module 30 such that the location of a user may be determined and referenced against the location of the capable providers in the provider database 18 in order to provide a listing of nearby capable providers to the user. For example, the providers may be filtered based on a location parameter (e.g., radius of 5, 10, 20 miles) and/or may be ordered for presentation based on proximity. In this regard, the user can input the symptoms that are presenting and in turn can be provided actionable information including an appropriate medical facility that is nearby and capable of treating the possible disease or conditions of the user.

Figure 3:
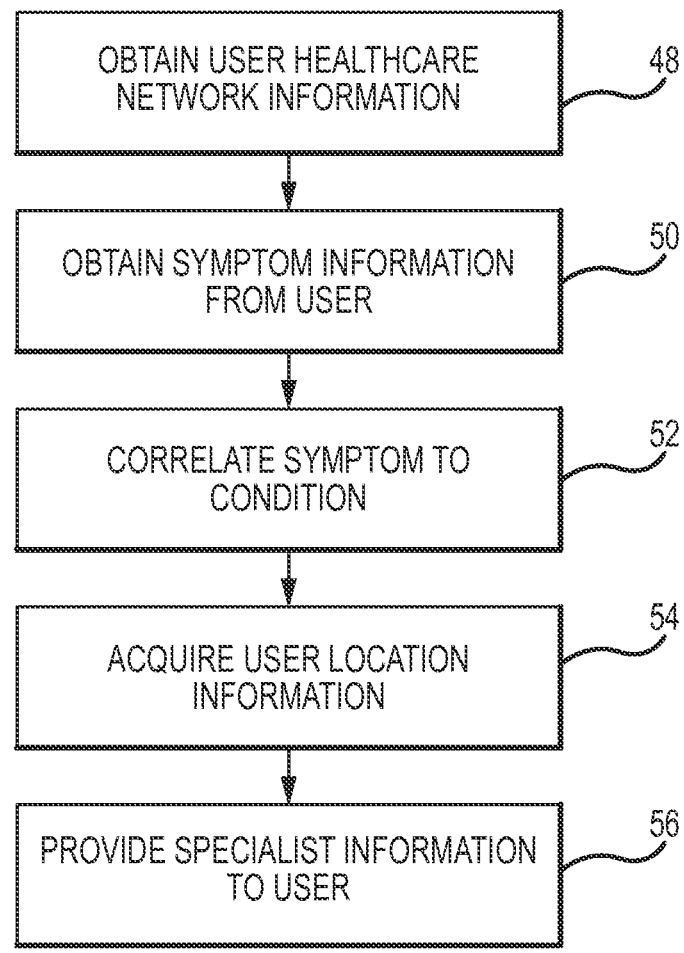
FIG. 3 is a flowchart depicting a further method in accordance with the present invention.

Turning to FIG. 3, an additional process in accordance with the invention is depicted using a flowchart. In FIG. 3, the user device 10 and/or other platform obtains (48) user healthcare network information. This may include information about a user's insurance provider or plan information. The healthcare network information may be obtained from the user directly, by way of logging into a healthcare network's website, or other means of obtaining user healthcare network information. The user provides (50) the user device 10 symptom information corresponding to a symptom of the user. The user device correlates (52) the selected identified symptoms to possible conditions or diseases that present the symptoms provided (50). Additionally, the user device may acquire (54) user location information, for instance by way of the location determination module 30. The user device may provide (56) specialist information to the user regarding the possible diseases or conditions correlated (52) to the symptoms. This specialist information may be tailored to both an appropriate provider that is within the user's healthcare network as well as one that is nearby. In this regard, the user device may provide the user information about local medical facilities that are capable of treating the disease or conditions from which the user may be suffering as well as providing information about providers or healthcare facilities in the user's network.

A description of certain functionality of the invention will now be presented in the context of an application executed on a user device 10 wherein the user device 10 is embodied in a mobile device, such as a cell phone with internet and location services. While user device 10 is shown as being executed on a mobile device, it is to be understood that similar or the same functionality may be provided in other types of user device executions such as a user device embodied as a desktop computer, laptop computer, or other device.

Figure 4:
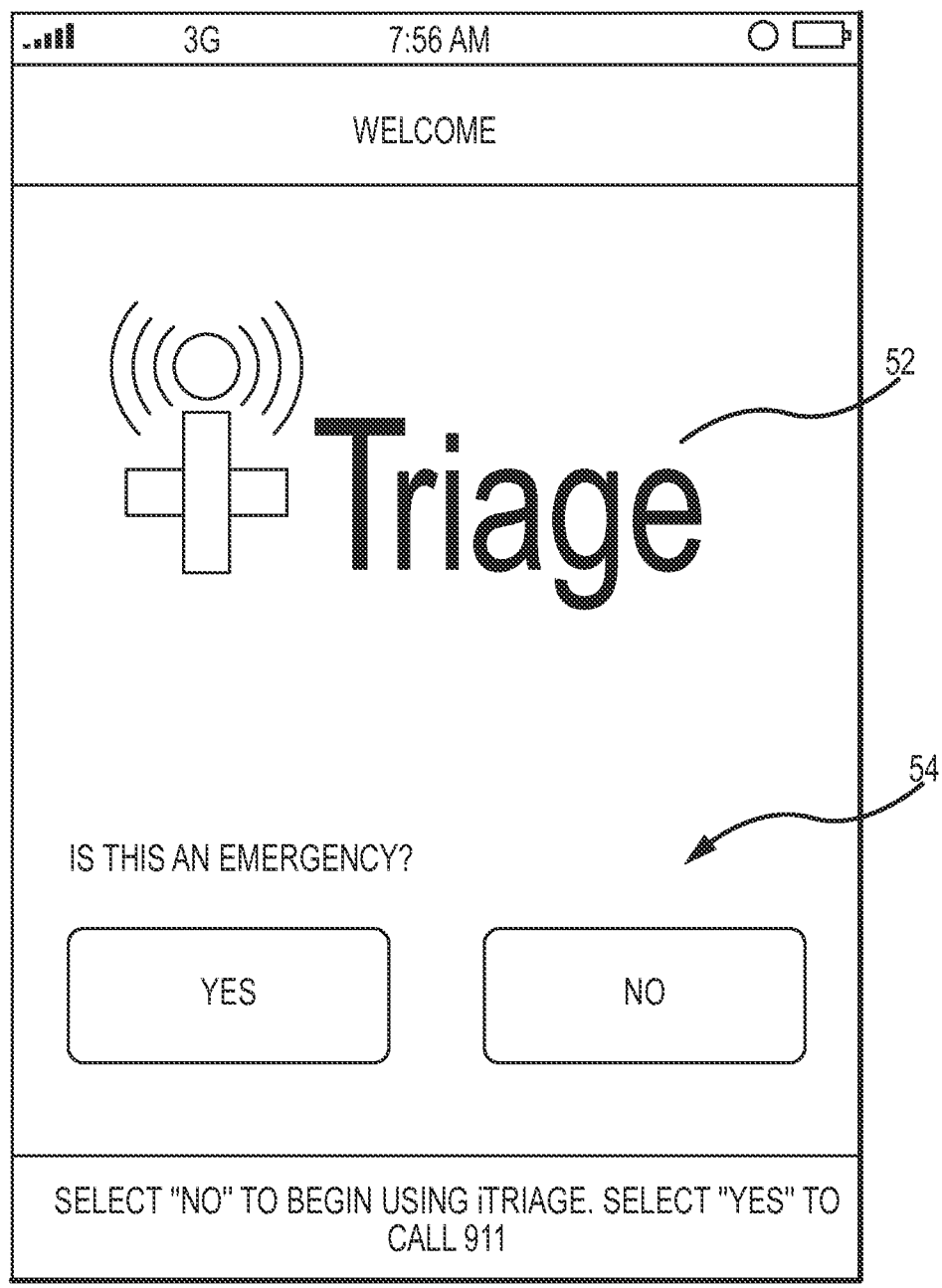
FIGS. 4-28 are screen shots illustrating various functionality in accordance with the present invention.
Figure 5:
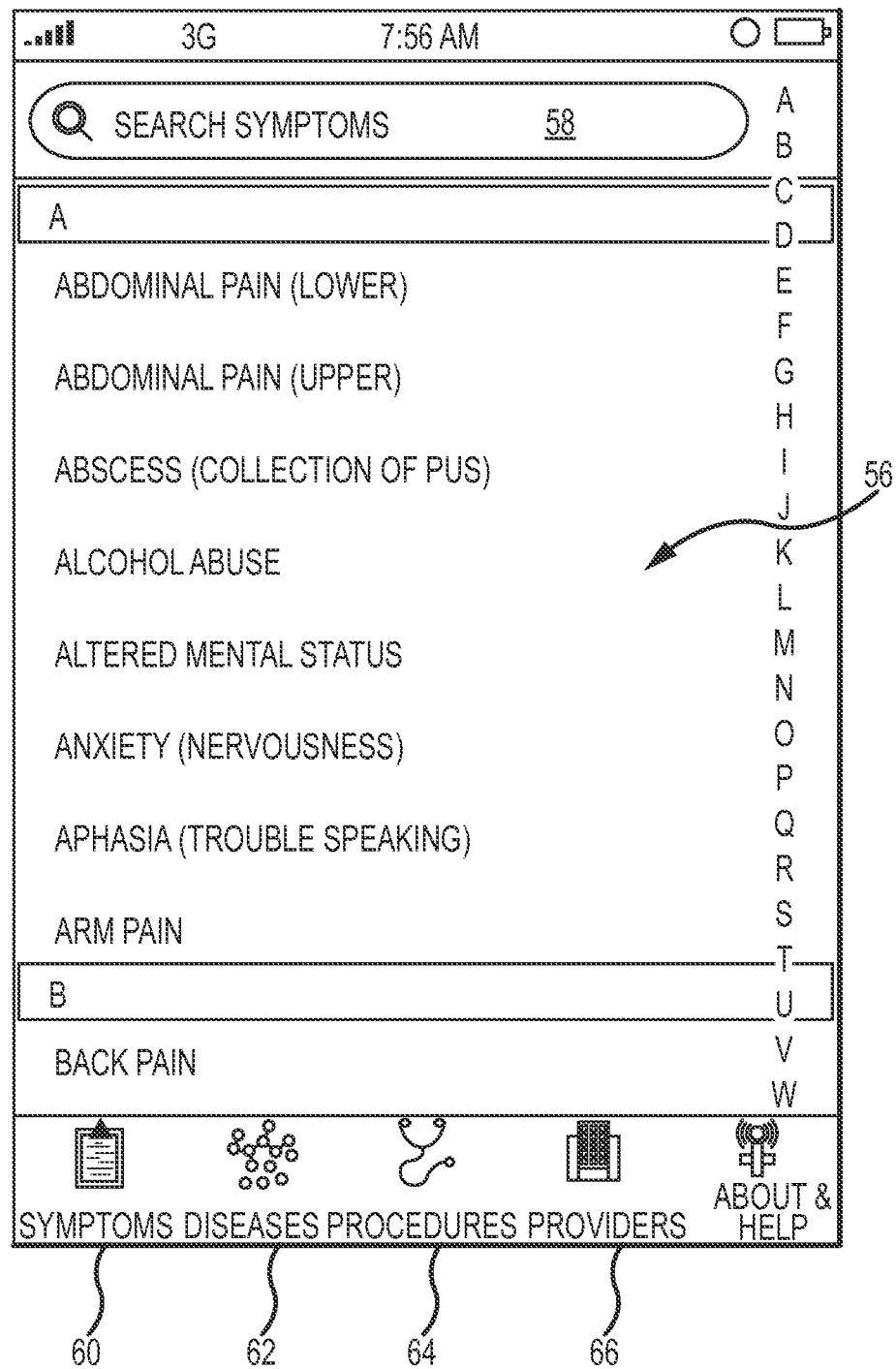

In FIG. 4, the user device may initialize a computer program and present to a user a welcome screen 52. The welcome screen 52 may include a capability of allowing the user to indicate whether the condition from which they are suffering is an emergency. This emergency selection 54 may consist of simply asking the user if the situation for which they are seeking information as an emergency. If the condition does comprise an emergency, the user may select "Yes" such that the mobile phone on which the program is running may activate the telephone network of the phone in order to dial an emergency number, such as 911. Alternatively, the user may select "No," such that the program proceeds. As can be seen in FIG. 5, a symptoms list 56 may be presented to the user after the initial welcome screen 52 and emergency selection 54. The symptoms list 56 may include a listing of all the database entries for items in the symptoms database 16 corresponding to diseases or medical conditions. The symptoms may be sorted by alphabetical order, or by category or other intuitive organization, to allow the symptoms to be found more easily. The symptom list 56 may include a lay description of the medical symptom as well as or instead of a medical description. Additionally, the symptoms may be searched by way of a symptom search box 58. The user may select any one of the symptoms 56 in order to be provided more information regarding that symptom.

Of note, in FIG. 5, navigation of the user device 10 may generally be facilitated by way of buttons or links presented in the user interface. A link may be presented for symptoms 60, diseases 62, procedures 64 and providers 66 such that these links may be used as shortcuts for users. For example, the symptoms list 56 may be accessed at any time by clicking on or selecting the symptoms link 60. Similarly, the other links may be used to navigate to other lists or information as will be discussed further below.

Figure 6:
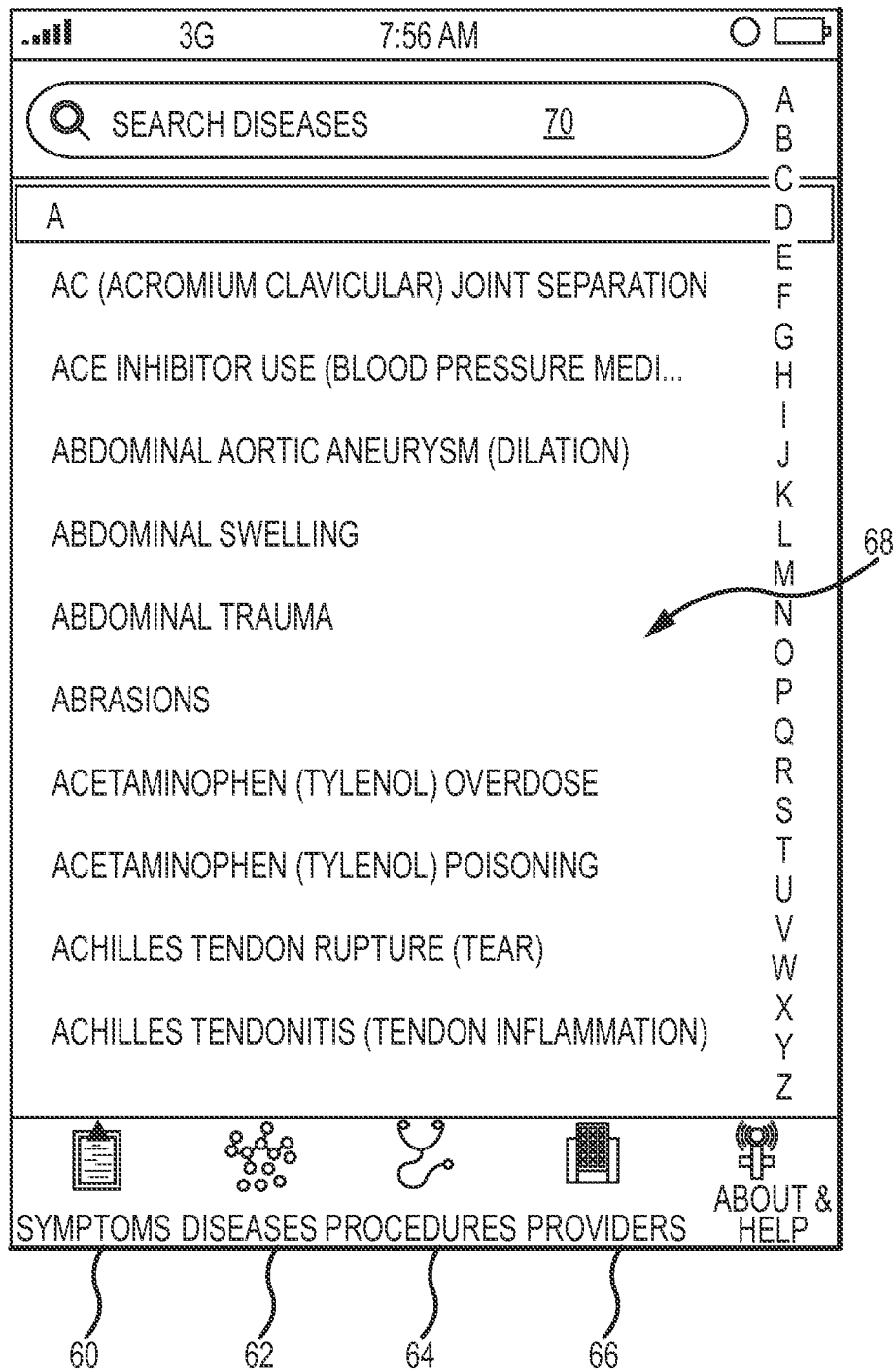

In FIG. 6 the diseases link 62 has been selected by the user such that a disease list 68 is presented to the user. Similar to the symptoms list 60, the disease list 68 may include a list of diseases or medical conditions contained in the disease database 14. Again, the diseases may be sorted by alphabetical order such that the diseases may be found more easily or alternatively a disease search box 70 may be provided. In this regard, the user may navigate the list of diseases contained in the disease database 14 in order to select a disease of interest to the user.

Figure 7:
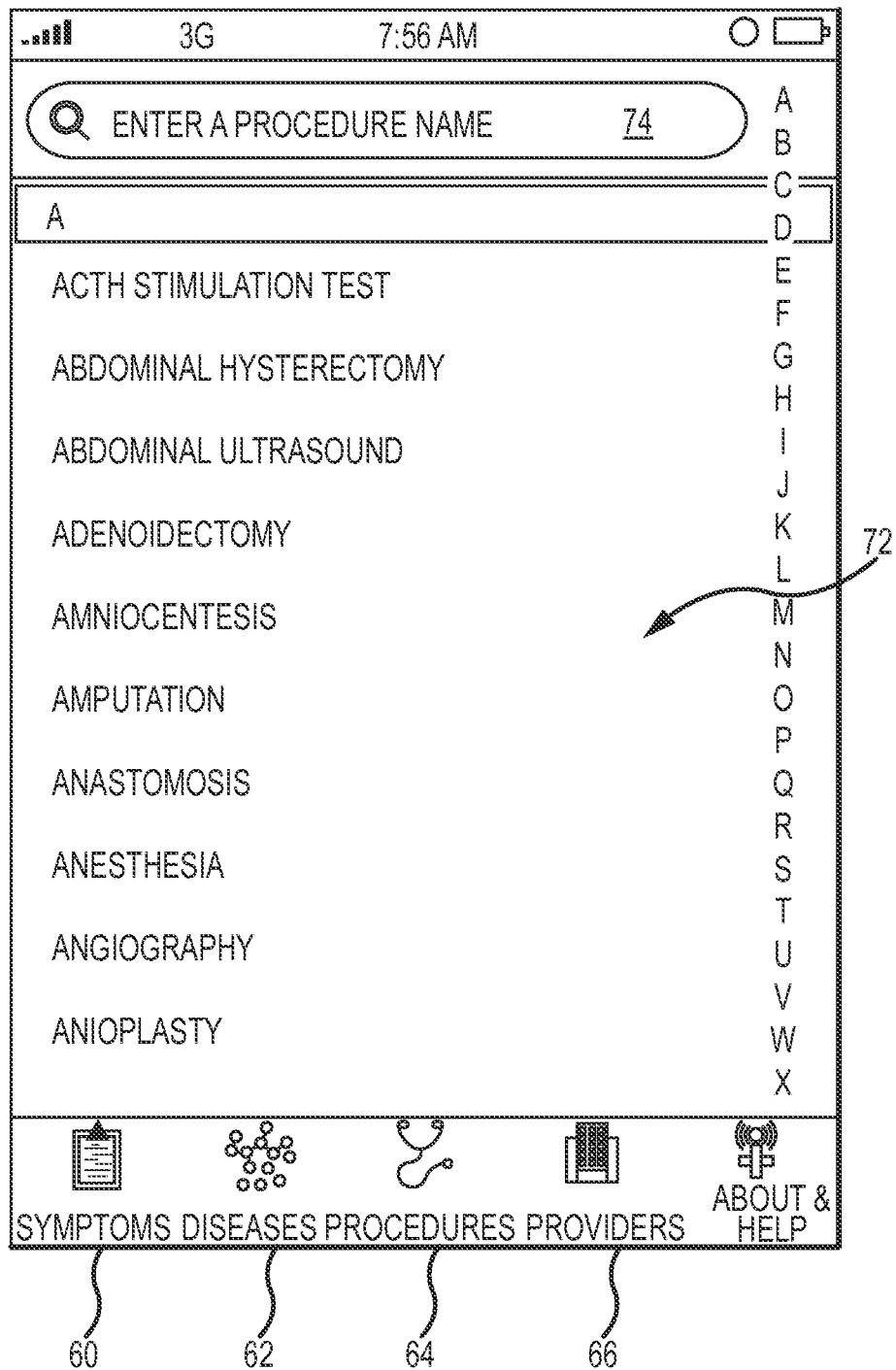

In a similar manner, FIG. 7 shows the screen displayed when the procedure link 54 is selected such that a procedure list 72 is presented to the user. Again, the procedure list 72 may contain a listing of entries of the procedure database 12. The procedures list 72 may be arranged in alphabetical order such that the procedure may be found more easily. Alternatively, the user may search using procedure search box 74 in order to search for procedures of interest by name.

Figure 8:
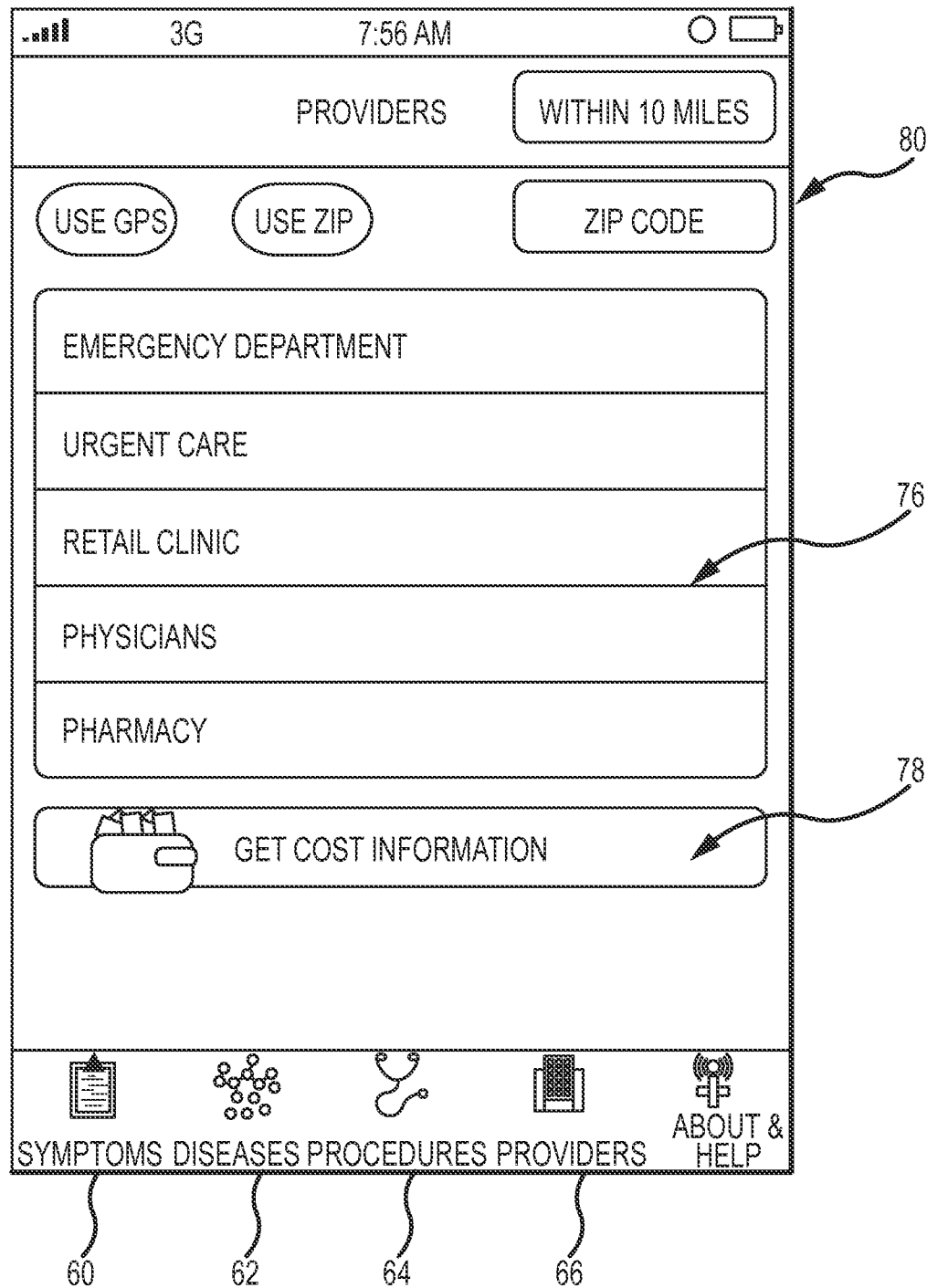
Figure 9:
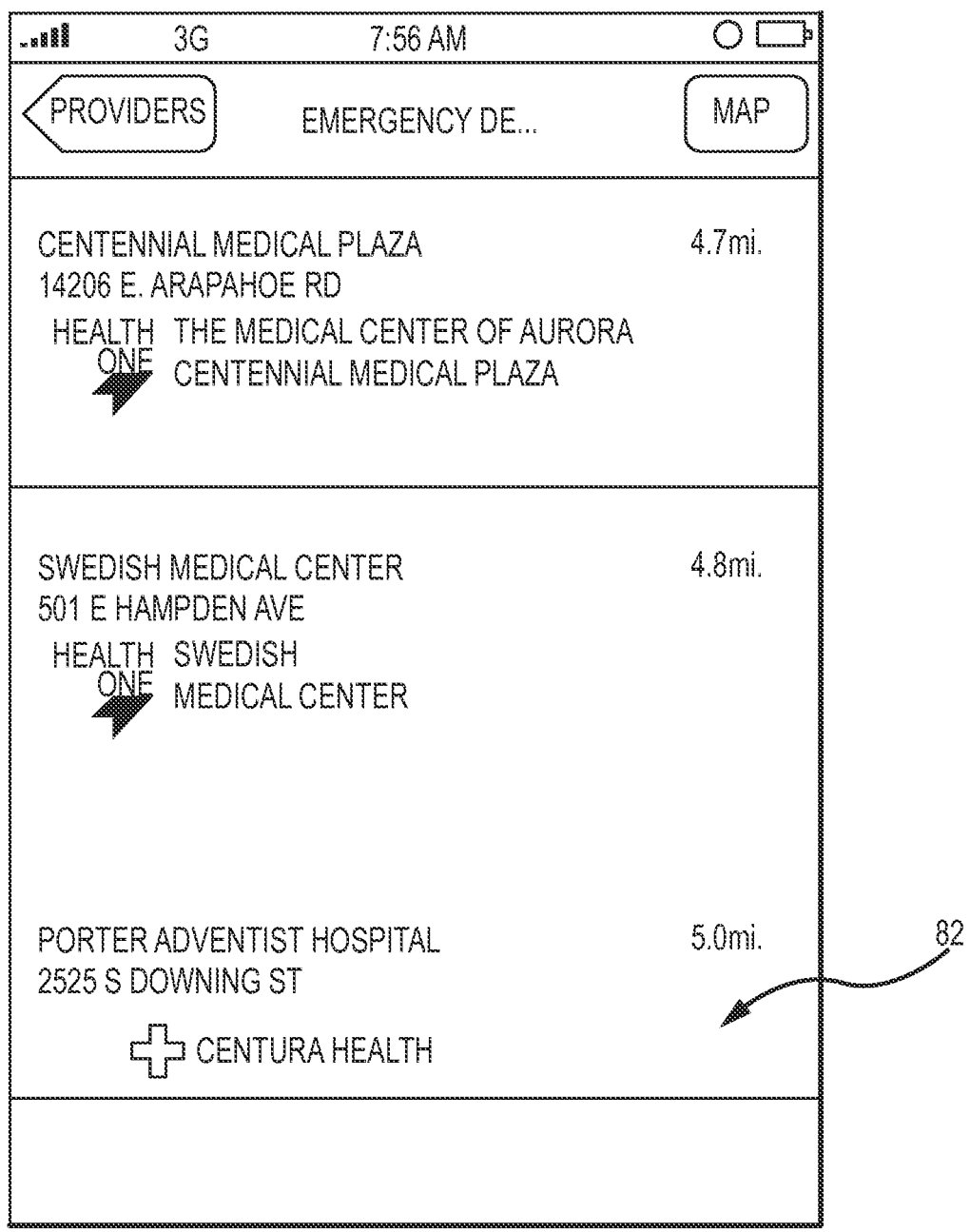
Figure 14:
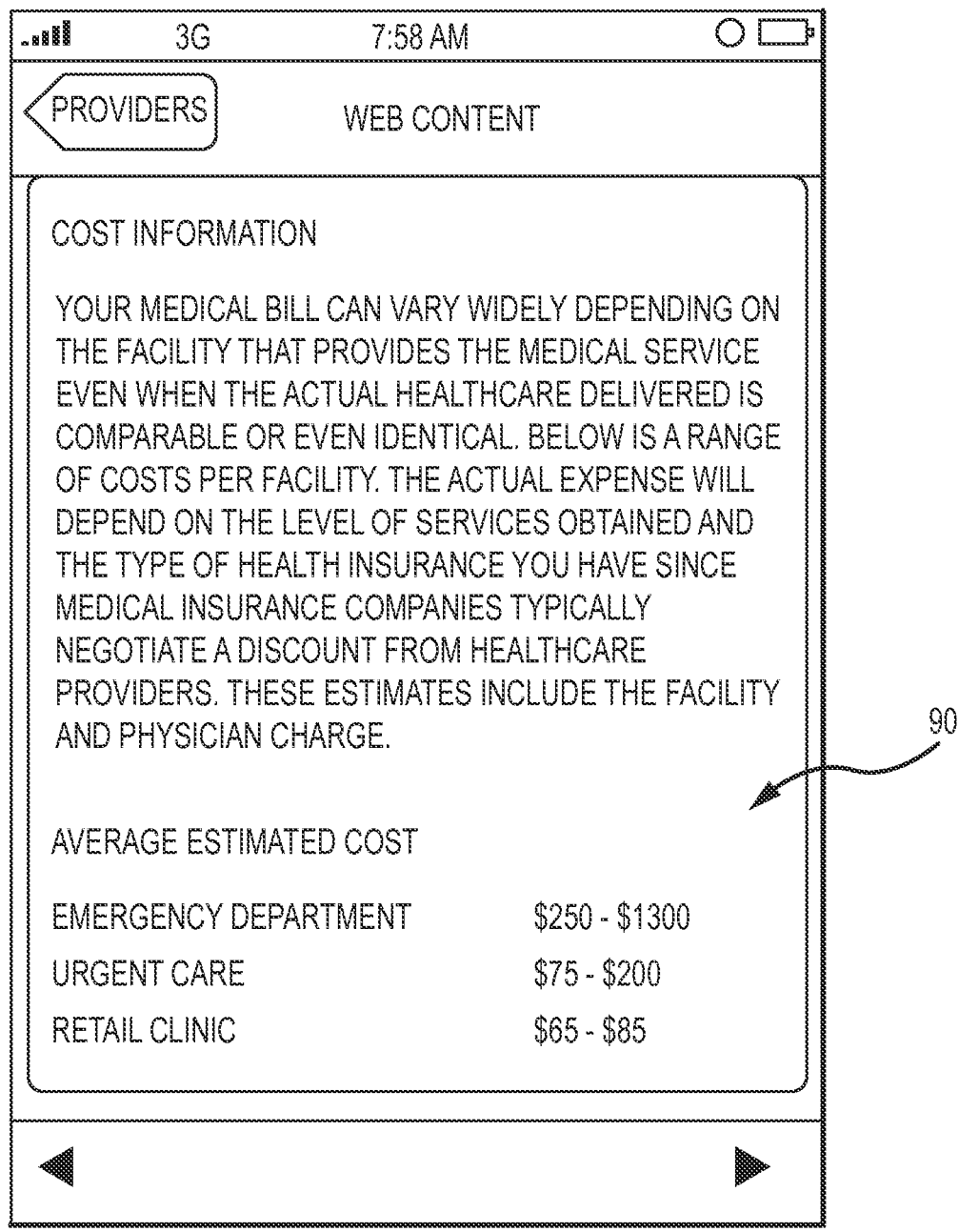

FIG. 8 shows a screen that may be presented to the user when the provider's link 66 is selected. The user may be presented a provider-type selection screen 76. Using the provider-type selection screen 76, the user may select from a variety of different healthcare provider types including, but not limited to; emergency departments, urgent care clinics, retail clinics, physicians and pharmacies. Users may also be presented with a cost information link 78 that may provide cost information regarding the different types of providers in the list 76 as shown in FIG. 14. Additionally provided in the provider's page link 66 may be a location services field 80. The user may be presented the option to provide a location (e.g., by way of a zip code input) or to use the location determining module 30 of the device to provide the user device 10 (e.g., integrated GPS receiver). Additionally, the user may selectively determine the search radius such that only providers within certain distances, (e.g., 10 miles, 20 miles, 50 miles or some other distance) may be displayed. As an example, in FIG. 9, provider list 82 corresponding to emergency departments within a 10 mile radius of the user may be displayed. That is, a provider's list 82 is populated with entries from the provider database 12 corresponding to emergency departments within a 10 mile radius of the user using the user device 10. The provider list 82 may sort by distance from the user.

Figure 10:
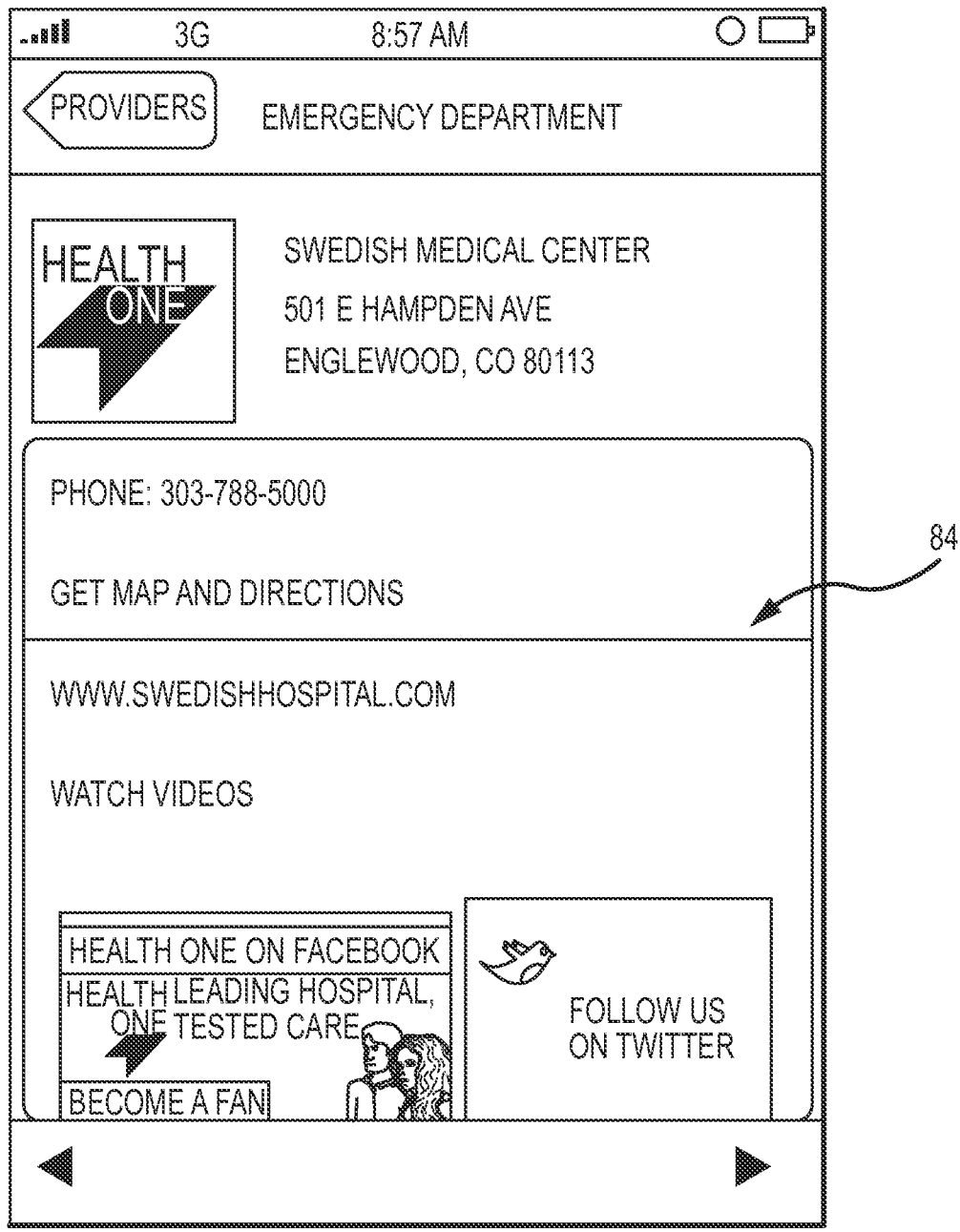
Figure 11:
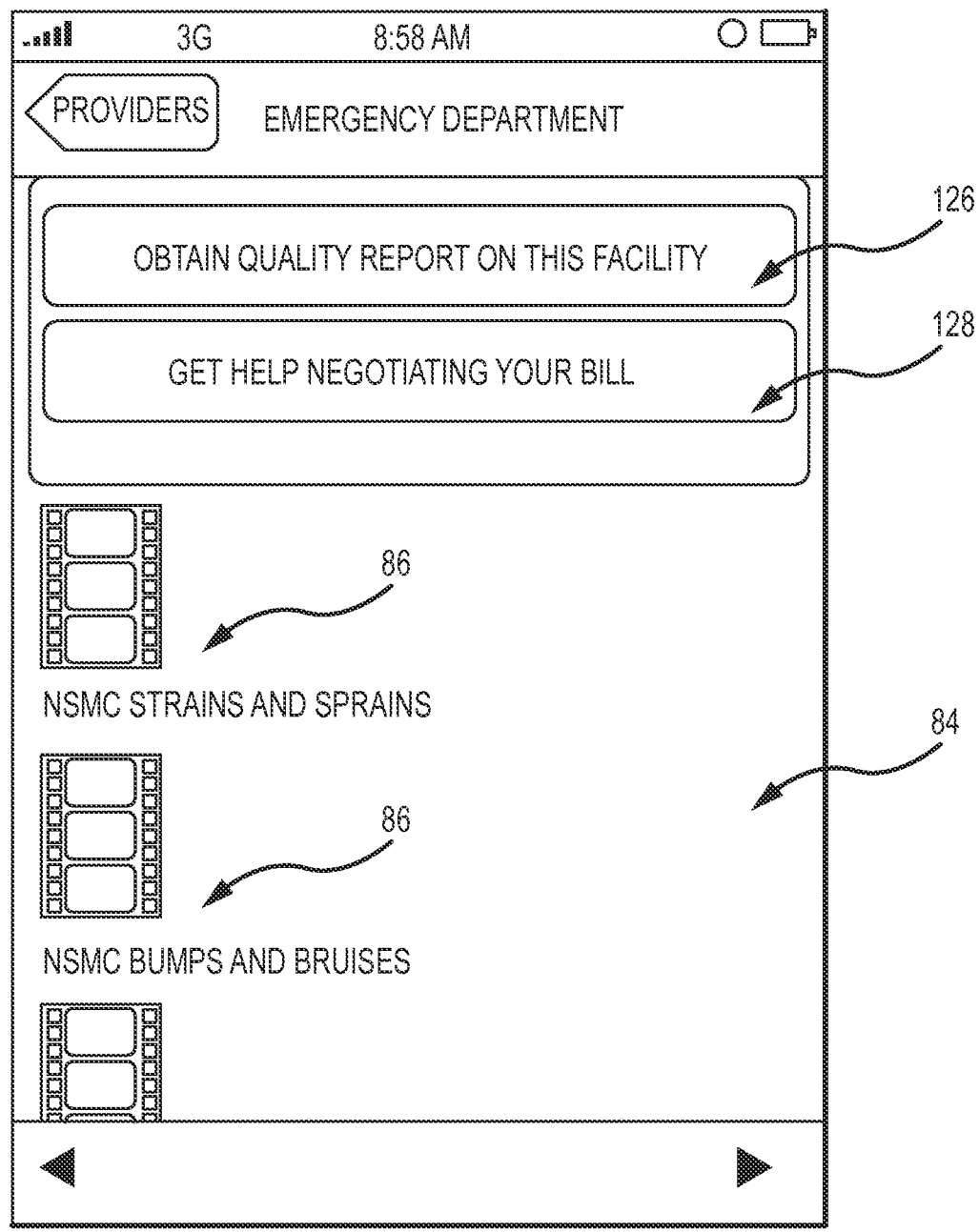
Figure 12:
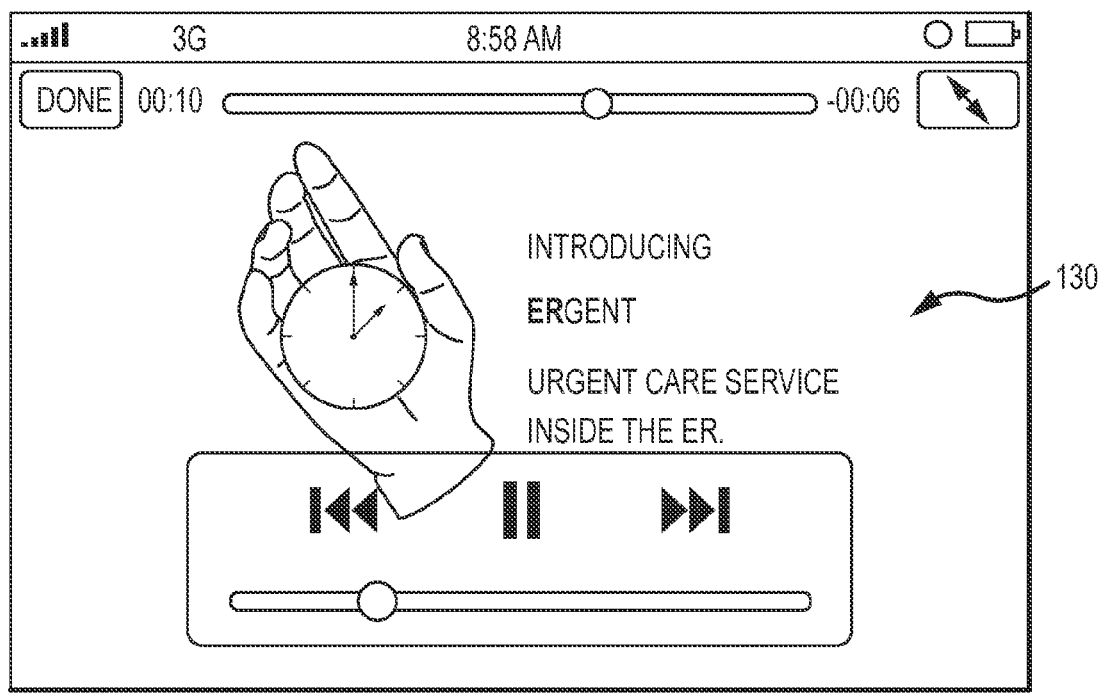
Figure 13:
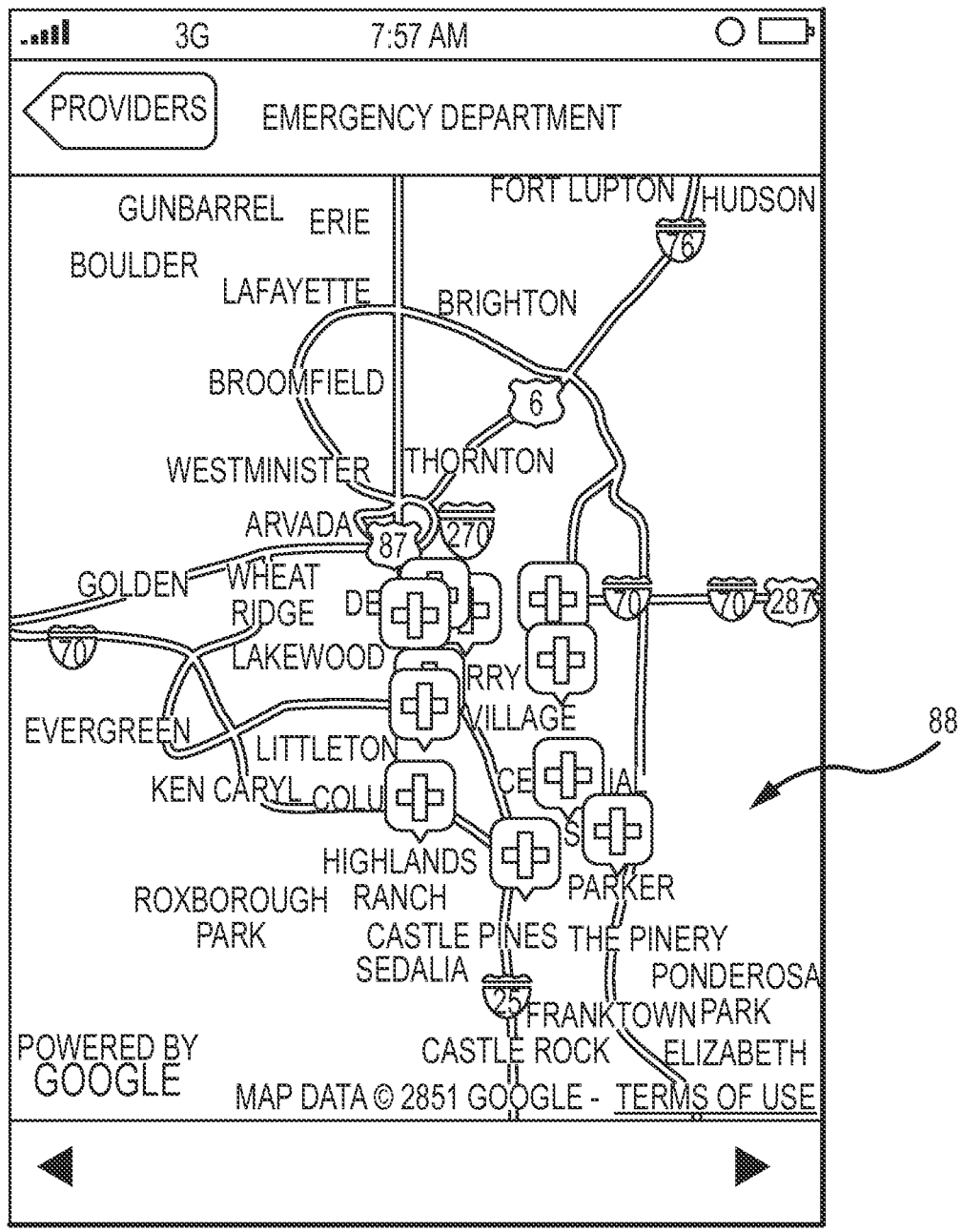

As seen in FIG. 10, a provider may be selected in order to obtain more information about a provider listed in the provider list 82. The provider information screen 84 may include information about the selected provider. This information may include the provider address; telephone number; the map and directions to the provider and the provider's website; or other information including, for example, informational videos, current wait times, staffing levels, etc. As can be seen in FIG. 11, the provider information screen 84 may also include a quality report links that may be used to direct the user to information about the selected provider. There may also be provided a cost negotiation link to information regarding negotiating a bill from the selected provider. Also listed on the provider information screen 84 may be one or more links to a series of videos 130 such as the one depicted in FIG. 12. In this regard, utilizing the user device 10, the user may access multiple sources of information including videos or other provider information. Of note, the provider information may further include a map 88 as seen in FIG. 13 that may show the location of providers.

Figure 15:
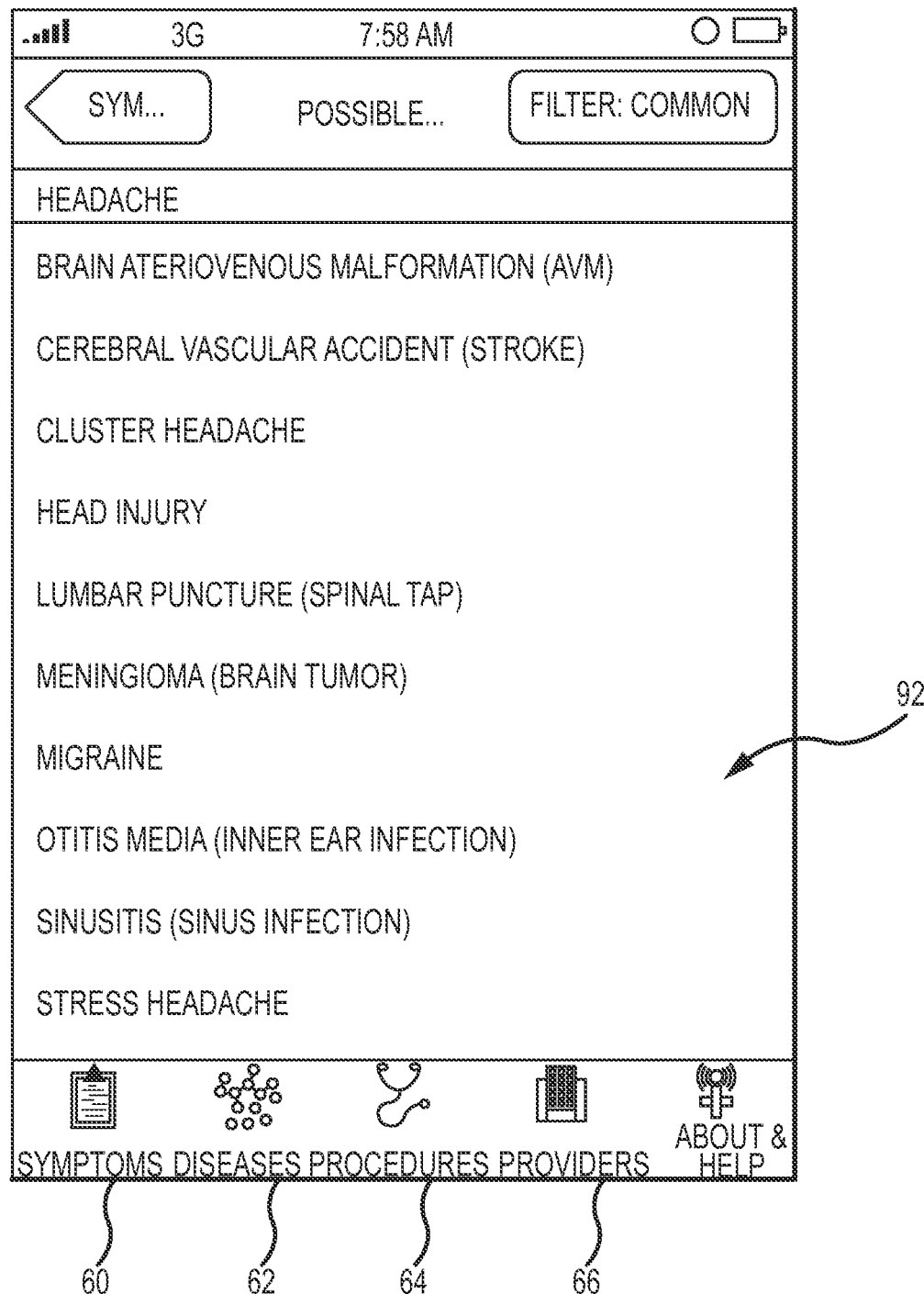
Figure 17:
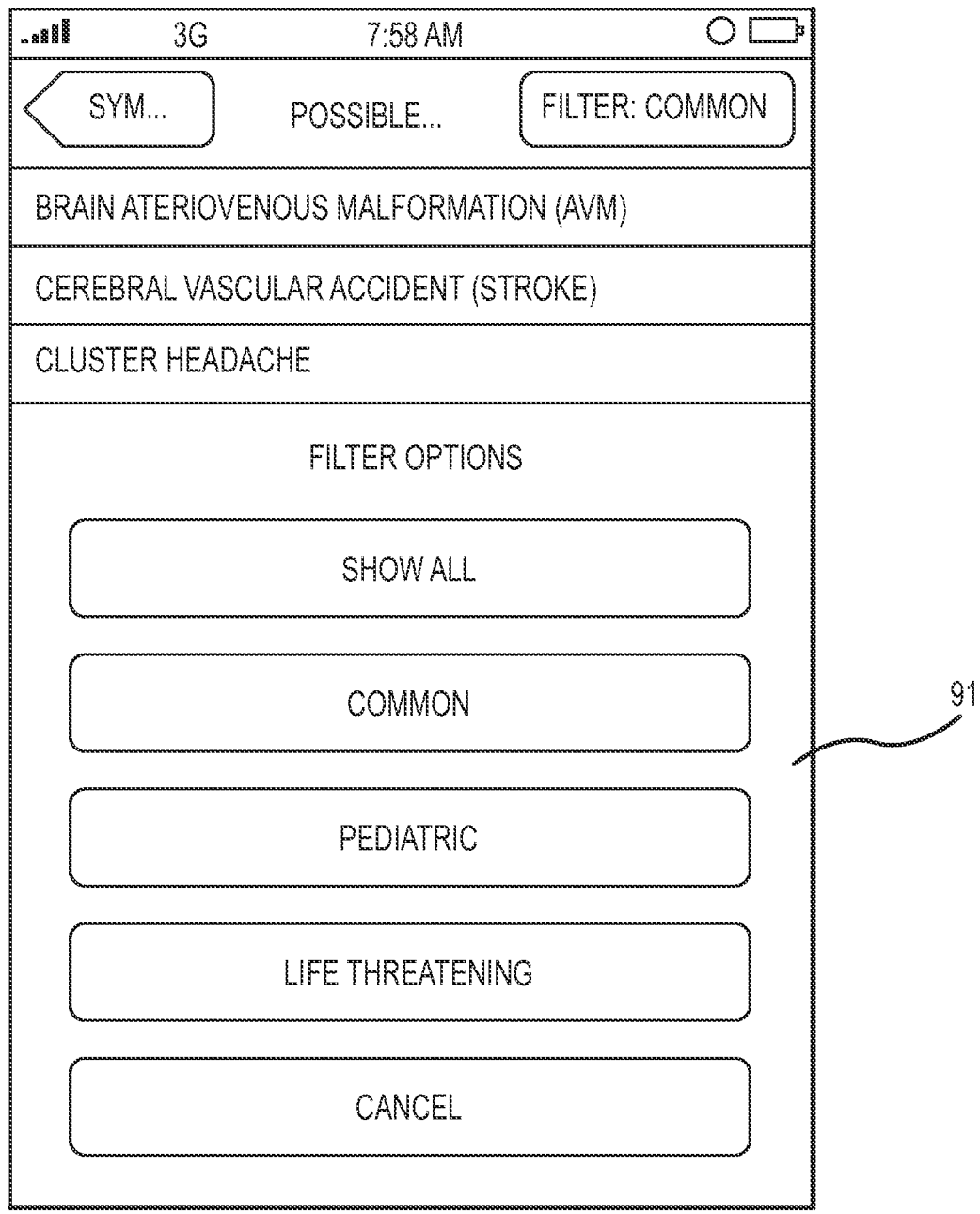

FIG. 15 shows a disease correlation list 92. The disease correlation list 92 may be presented after a user selects a symptom from the symptoms list 60 corresponding to a symptom which they may be presenting. For instance, in FIG. 15, the symptom "headache" has been selected from these symptoms list. Accordingly, some possible medical conditions associated with a headache maybe represented to the user in a disease correlation list 92. From the disease correlation list 92, the user may select a disease from the list of diseases or medical conditions associated with the symptom they may be presenting. FIG. 17 shows an option of the disease correlation list 92 wherein the diseases may be sorted by a variety of filters. For instance, the filter options may include filtering the diseases presented in the disease correlation list 92 into disease classes corresponding to common diseases, pediatric diseases, or life threatening diseases. In this manner, the diseases included in the disease correlation list 92 may be sorted by a variety of options by the user.

Figure 16:
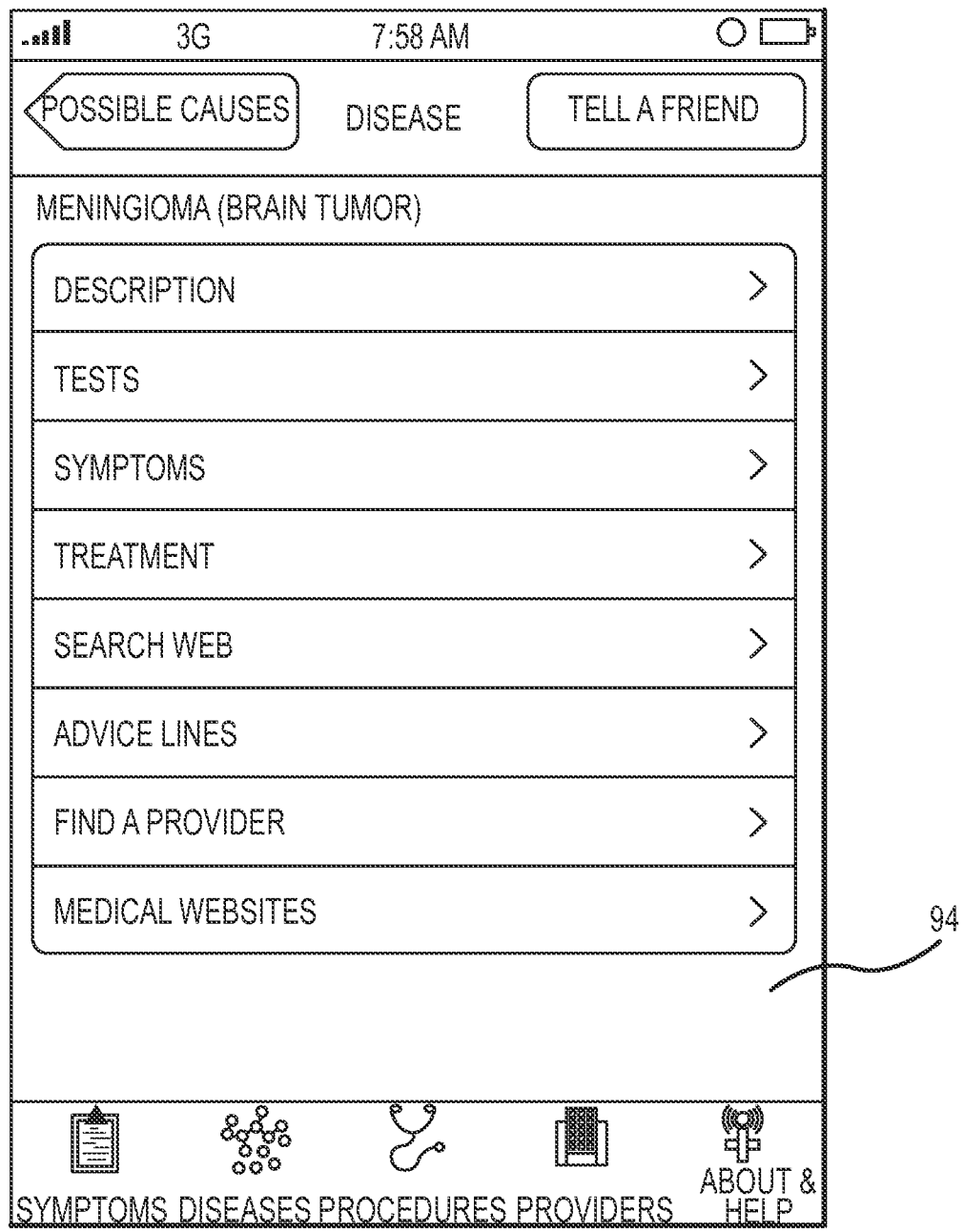

With further reference to FIG. 16, the user may have selected meningioma (brain tumor) from a disease list, for example. In this regard, a disease information screen 94 may be presented to the user. From the disease information screen, the user may select from a variety of information listings about the disease including, but not limited to, a description of the disease, possible tests to determine the existence of the disease, symptoms of the disease, as well as common treatments associated with the disease. Additionally, a plurality of links may be presented to the user, such as for instance, the ability to search the web with particular guided searches dealing with the selected disease, advice lines, provider list tailored to the disease, or other medical websites for which the user may obtain information.

Figure 18:
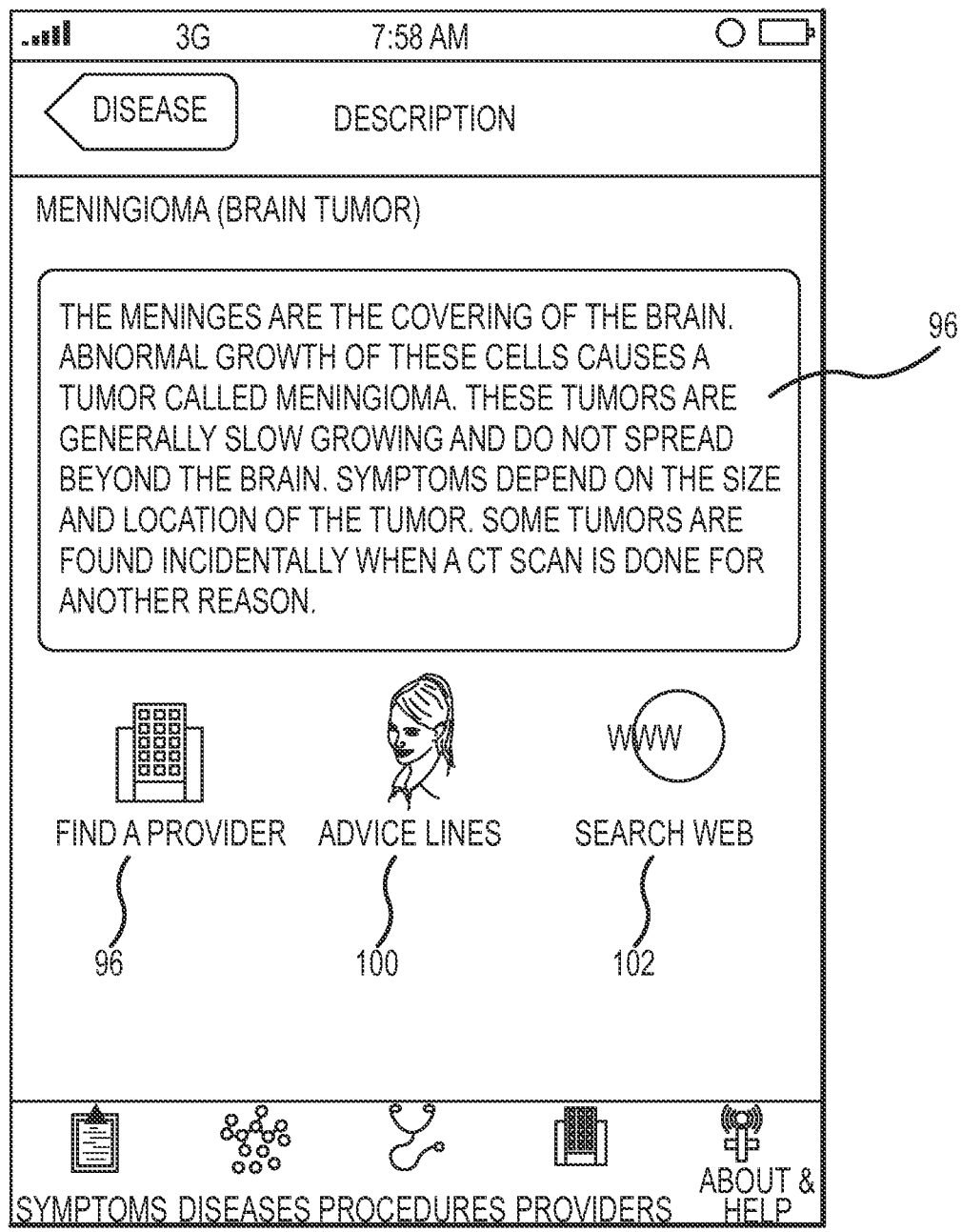
Figure 19:
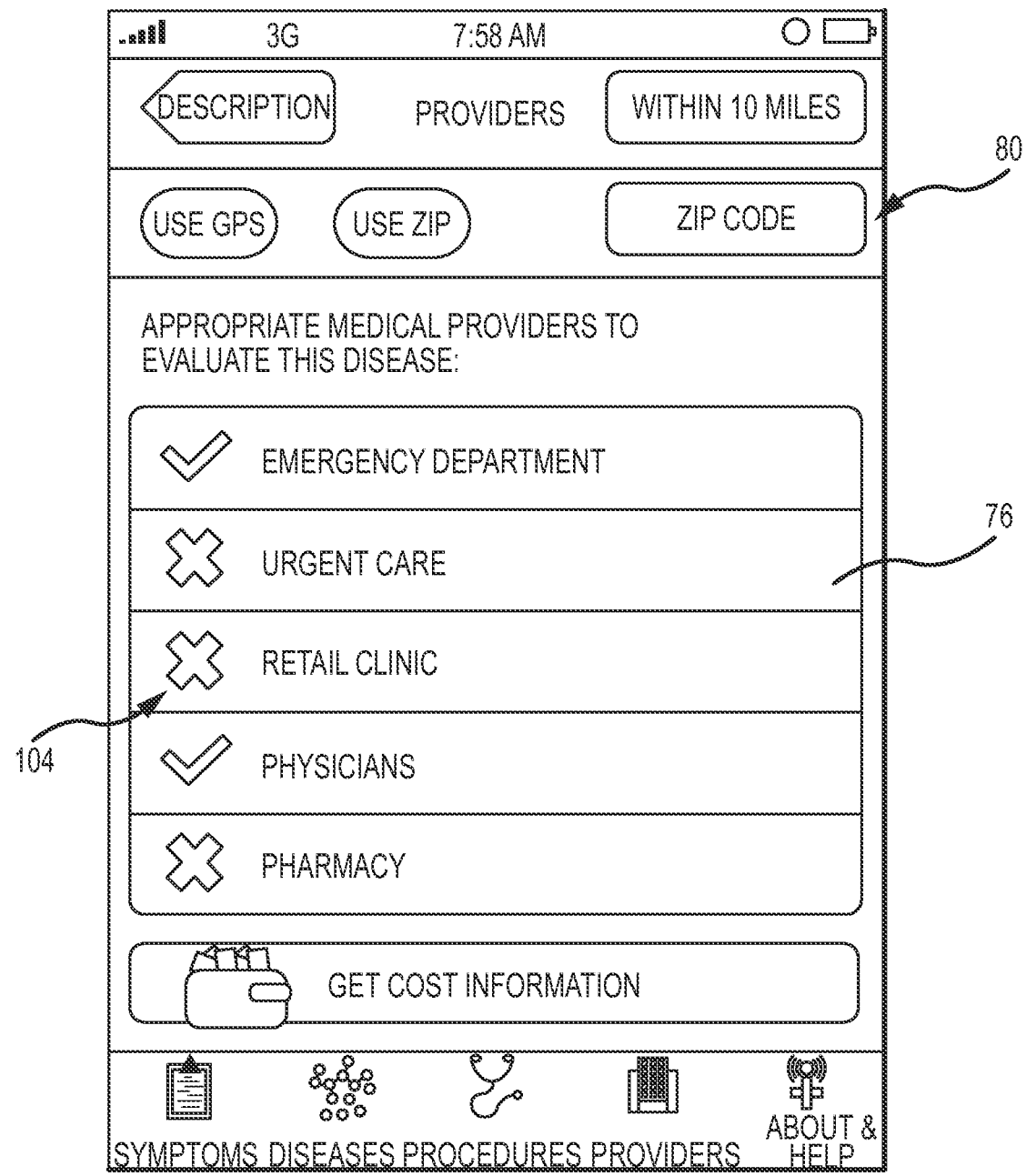

FIG. 18 shows a screen that may be presented to the user if the description option is selected in the disease information screen 94. The disease information screen 96 presents a brief description of the disease. Additionally, in the disease description screen 96 a plurality of options may be presented from which the user may choose. These may include a "Find or Provider" link 98, an "Advice Line" link 100 and a "Search Web" link 102. FIG. 19 shows a provider-type selection screen 76 that may be presented if the "Find a Provider" link 98 is chosen. As can be seen, the provider-type selection 76 may be similar to that shown with reference to FIG. 8, where the provider-type selection screen 76 was accessed from the provider link 66. However, the provider-type selection screen 76, when accessed from the finer provider link 98, may differ in that severity indications 104 related to the disease selected may be included. For instance, in FIG. 19, based on the severity of the disease selected (the brain tumor), indications may be presented to the user indicating the appropriate facility from which treatment could be rendered from the stratified list of providers based on the severity level each provider is equipped to treat. In the example shown in FIG. 19, the appropriate facility is designated by the severity indications 104 (e.g., emergency departments as well as physicians). Of note, also included in this provider screen may be a location services field 80 similar to the one presented in FIG. 8 wherein the user may manually input or rely on location services 30 of the user device 10 in order to provide location of the user.

Figure 20:
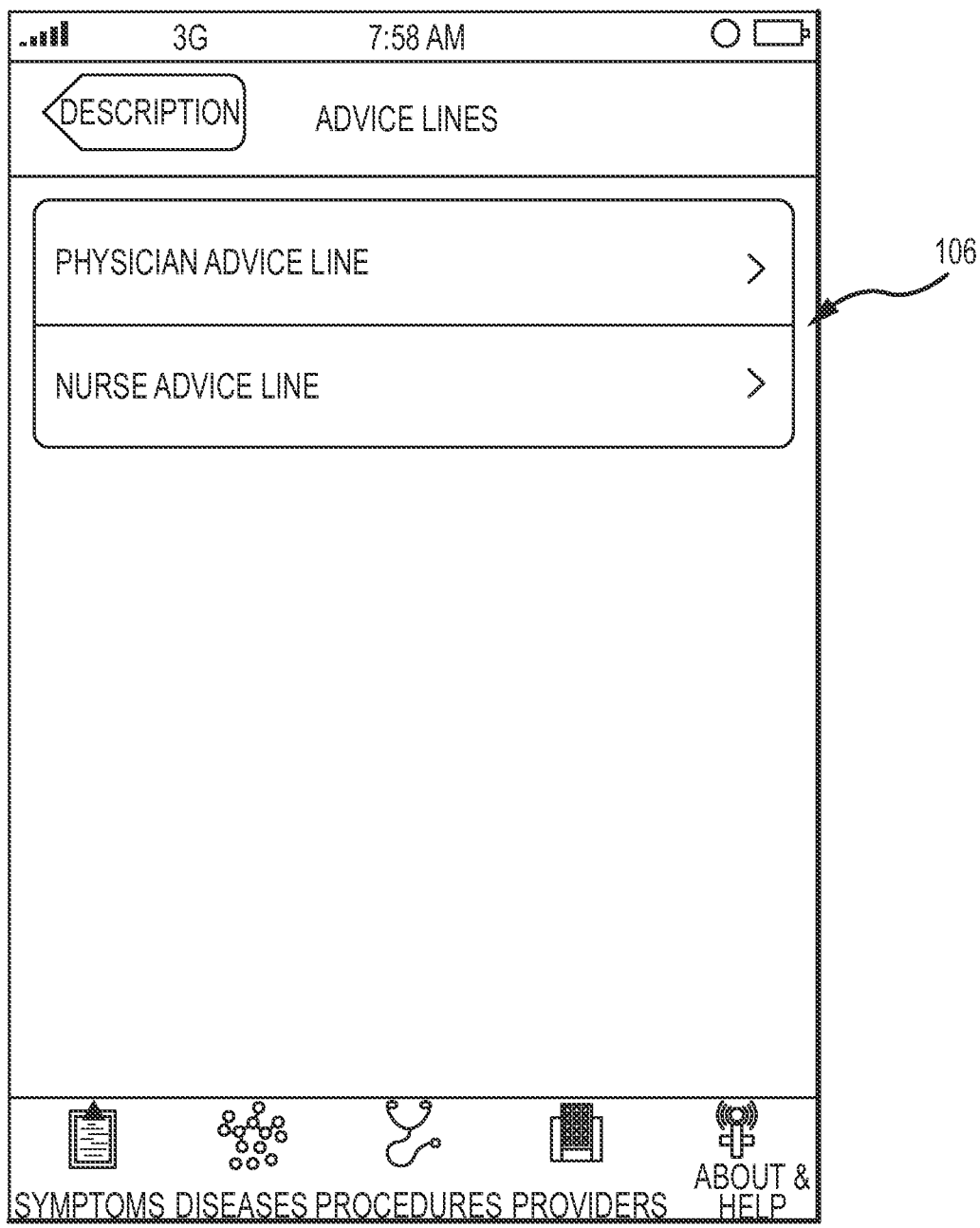
Figure 21:
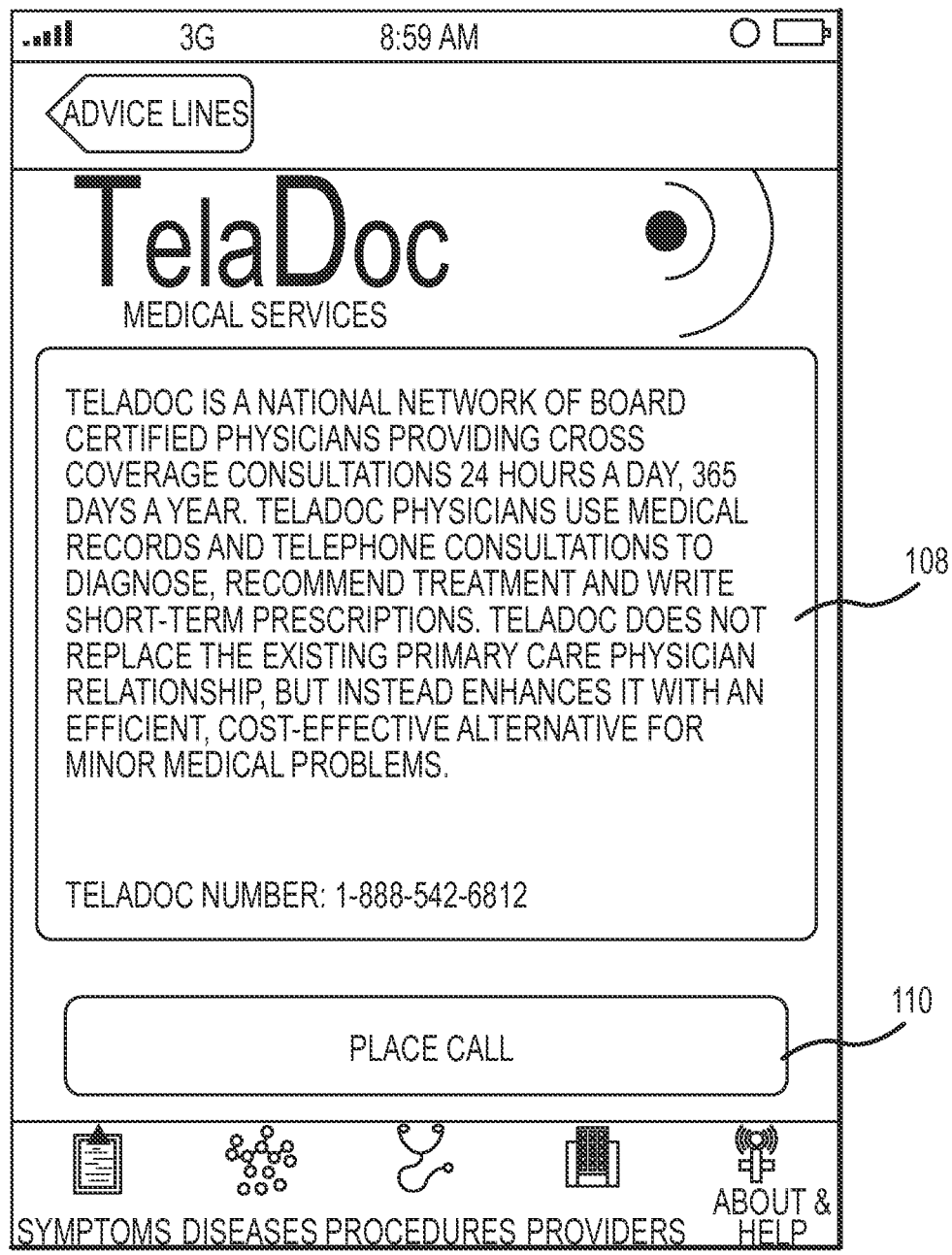
Figure 22:
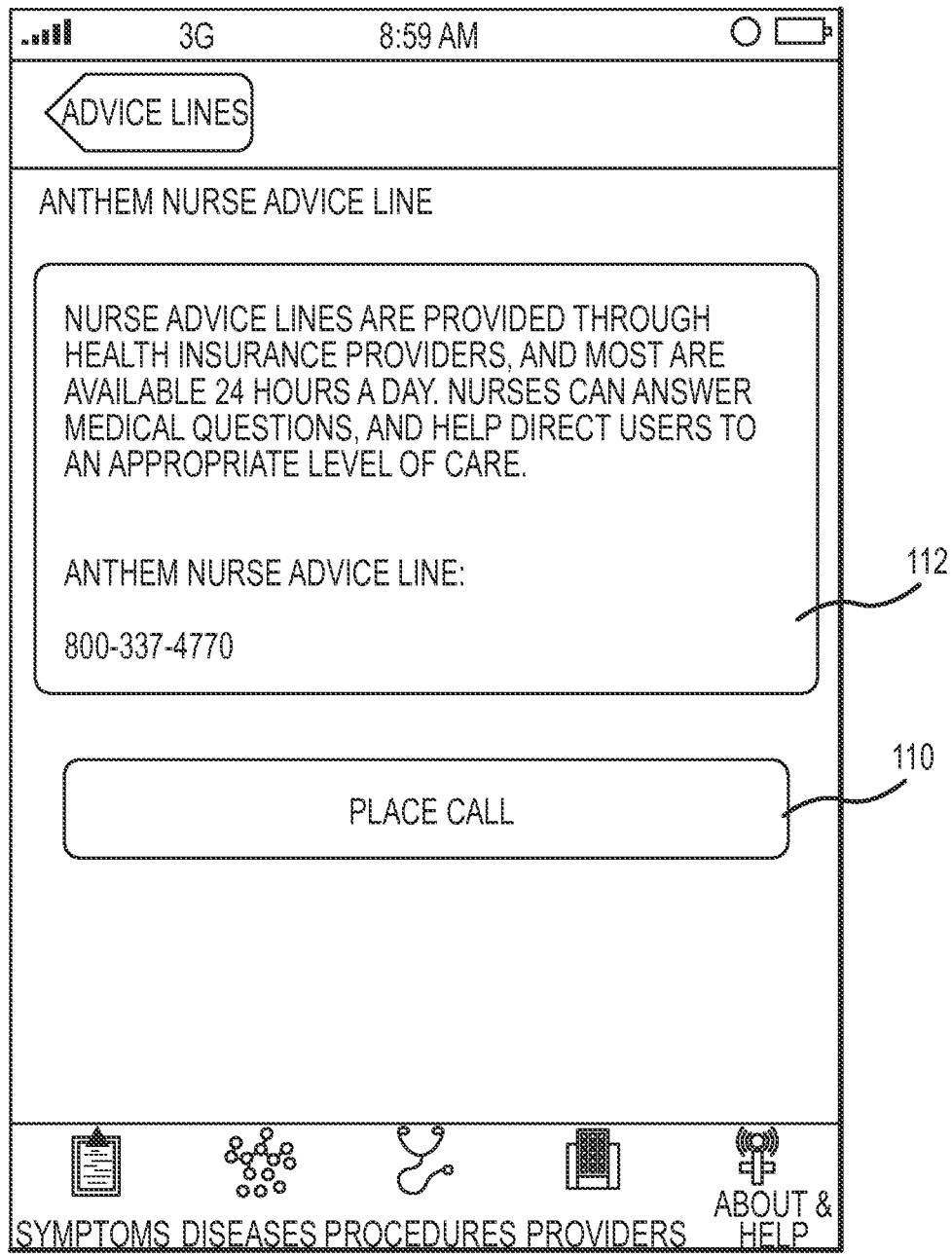

FIG. 20 includes an advice line screen 106 that may be accessed by selecting the "Advice Line" link 100 as shown in FIG. 18. When the user selects the "Advice Line" link 100, the user may be presented with two options. One may be to connect to the physician advice line, while the other option may include connected to a nurse advice line. FIG. 21 shows an embodiment of the physician advice line screen 108. For instance, the physician advice line 108 may include a description of the services provided by the physician advice line as well as a telephone number corresponding to the physician advice line. In this embodiment, a call link 110 may be provided wherein the telephone network 22 of the mobile device may be activated to place the call directly to the physician advice line. Alternatively, if the nurse advice line is selected in FIG. 20 from the advice line screen 106, a nurse advice line screen (shown in FIG. 22) 112 may be presented. The nurse advice line screen may similarly contain a call link 110 enabling the user device 10 to activate the telephone network 22 of the mobile device in order to dial the nurse advice line. The nurse advice line screen 112 may differ from the physician advice line screen 108 in that the nurse advice line screen may be based on the health network information provided by the user. As can be seen, the nurse advice line screen 112 may include information specific to the designated healthcare provider. As such, the user may have indicated or obtained information regarding a health care network. In this regard, when the nurse advice line screen is presented 112, the number for the device line may be particularly directed to the network in which the user is provided service.

Figure 23:
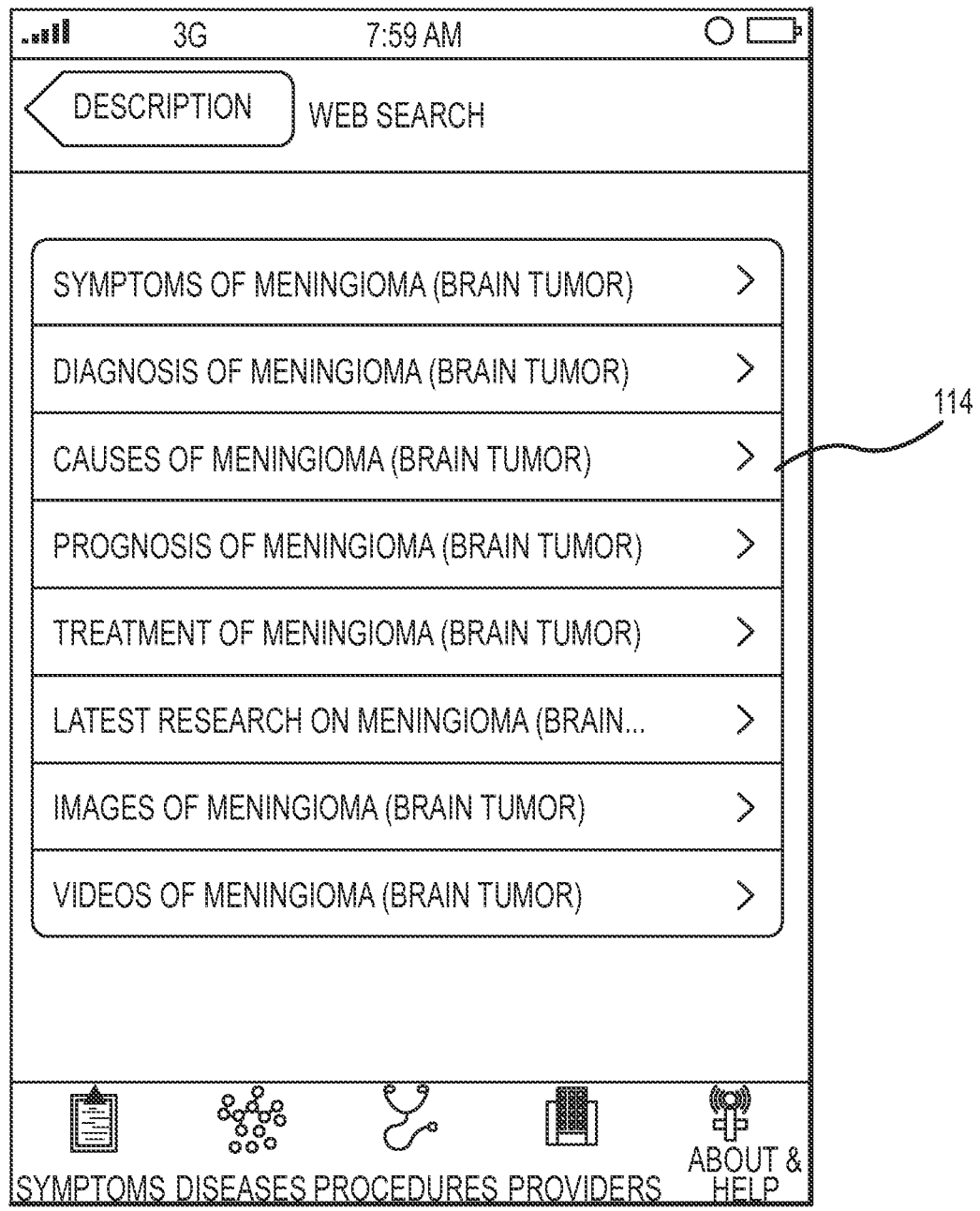

FIG. 23 includes a web search screen 114 that may be displayed to the user when the web search link 102 is selected. The web search screen 114 may include a plurality of pre-defined web searches based on conditions identified in the disease information screen 94. For instance, the plurality of pre-defined web searches may include symptoms of the disease, a diagnosis of the disease, causes of the disease, prognosis of the disease, treatment of the disease, latest research on the disease, images of the disease or videos pertaining to the disease. As a result, a directed web search may be conducted by simply choosing one of the links presented in the web search 114. In this regard, the user device 10 may provide the user a directed web search capability such that specific pre-defined web searches may be correlated to a selected disease and may be presented to the user.

Figure 24:
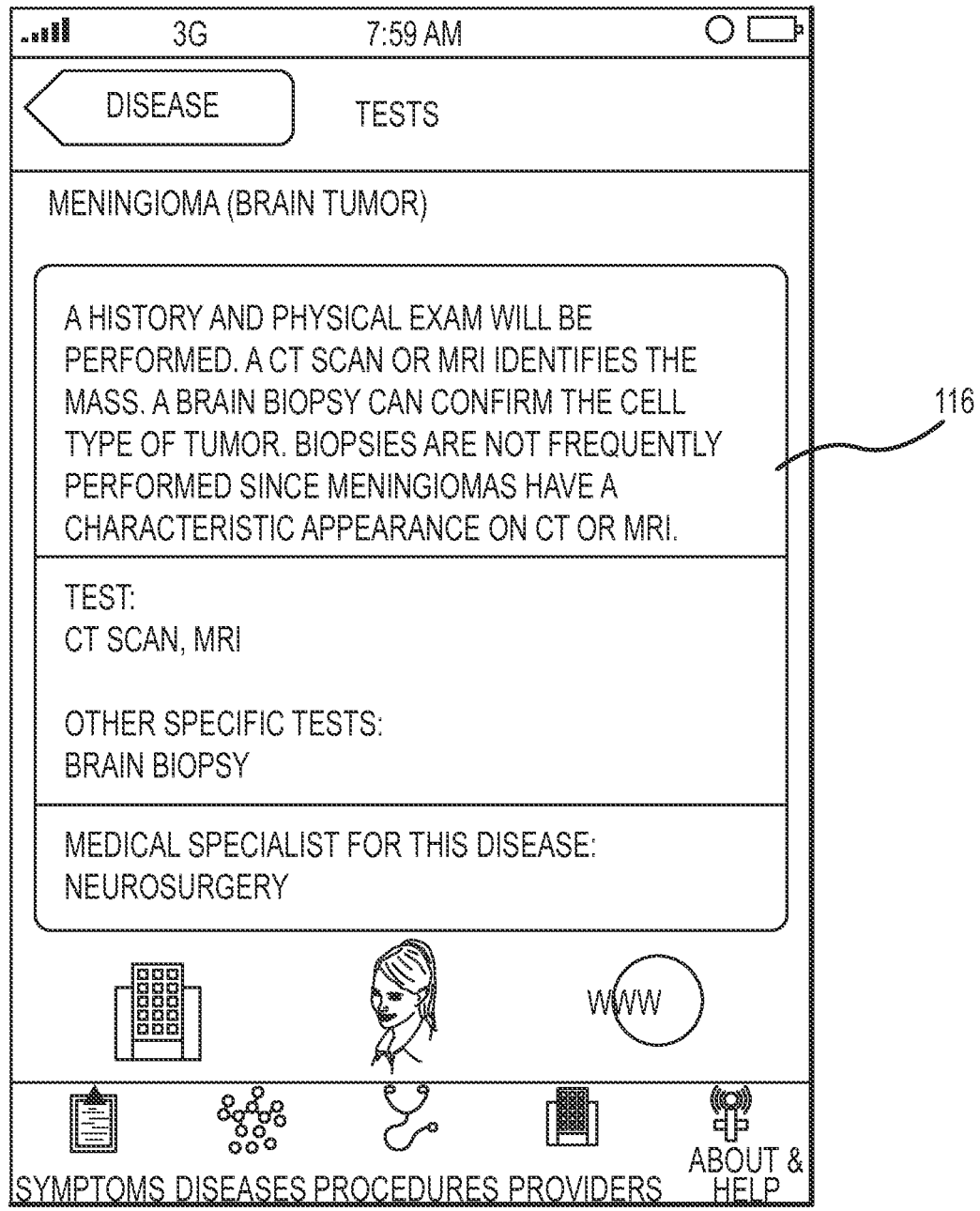

Returning to FIG. 16, on the disease information screen 94, the user may select a test link such that they are presented with a disease test screen 116. The disease test screen 116 (shown in FIG. 24) may include a description of tests or procedures undertaken in order to diagnosis or identify a selected disease. Also, a medical specialist corresponding to the disease may be included in the disease test screen 116 such that the user may readily identify a specialist in order to treat the disease that has been selected. This may allow a user to determine the specialist needed to treat the particular disease or condition that the user is researching. Accordingly, the user may restrict a provider search to this limited specialty as will be described further below.

Figure 25:
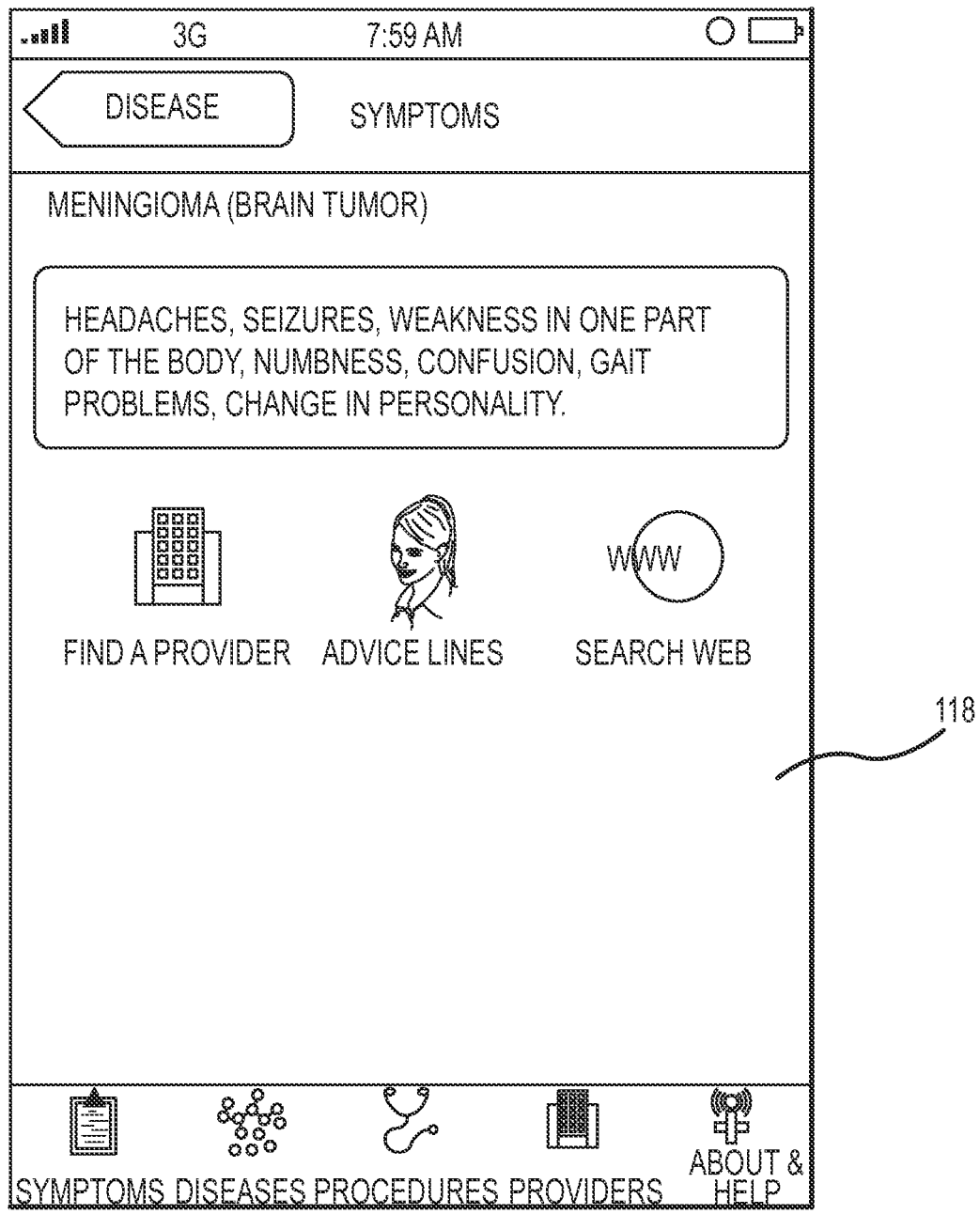

Additionally, from the disease information screen 94, the user may access a symptom screen 118. The symptom screen 118 (shown in FIG. 25) may present the user with a list of common symptoms associated with the selected disease identified in the disease information screen 94.

Figure 26:
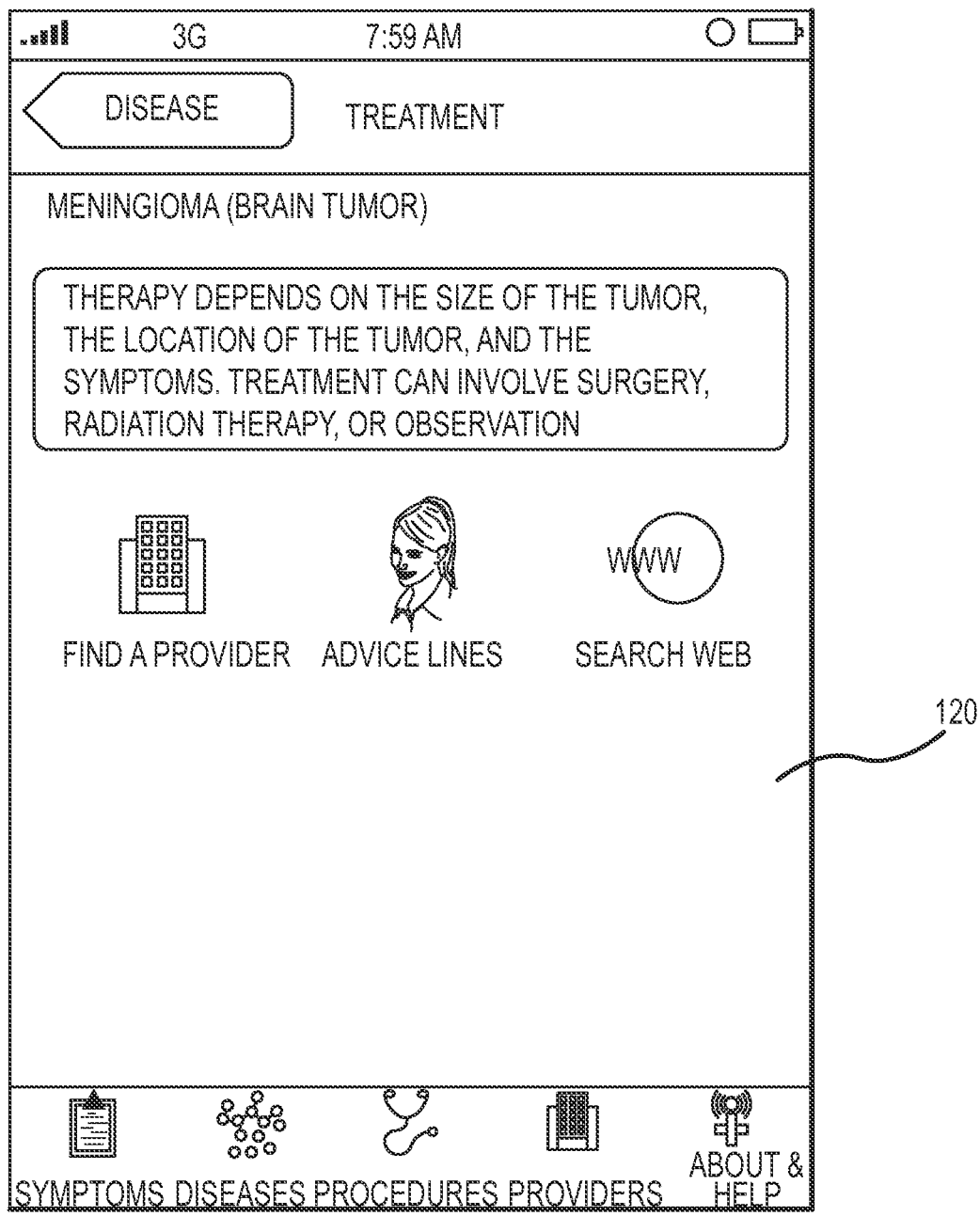
Figure 27:
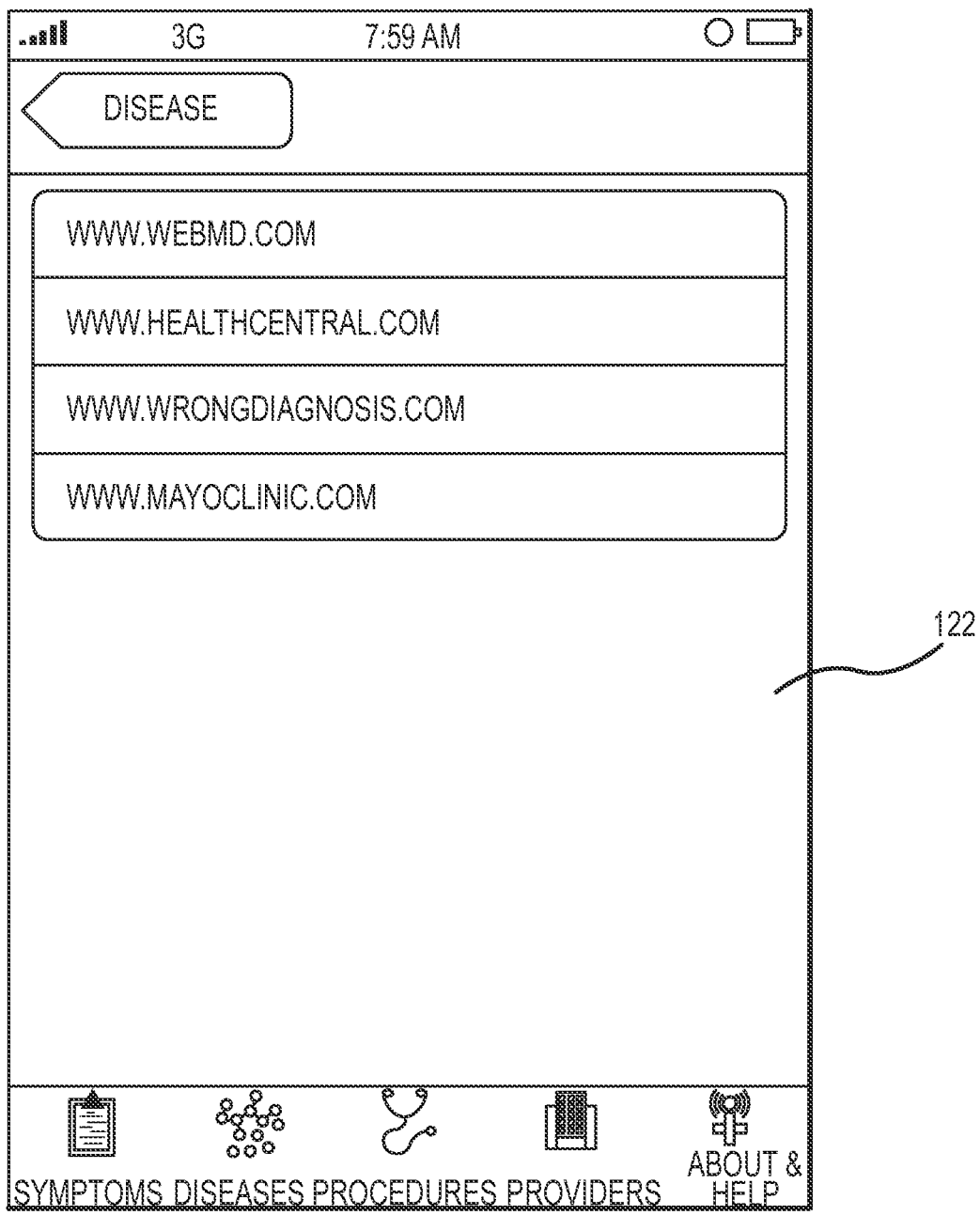

Alternatively, the user may select from the disease information screen 94, a disease treatment screen 120 (shown in FIG. 26). The disease treatment screen 120 may present to the user a list of potential or possible treatments related to the treatment of the disease identified in the disease information screen 94. Alternatively, a web resources screen 122 may be presented by selection of the disease information screen 94. One such example of a web link information screen 122 presented in FIG. 27. As can be seen in FIG. 27, the web link information screen 122 may include a plurality of links to online resources containing information about the disease selected in the disease information screen 94.

Figure 28:
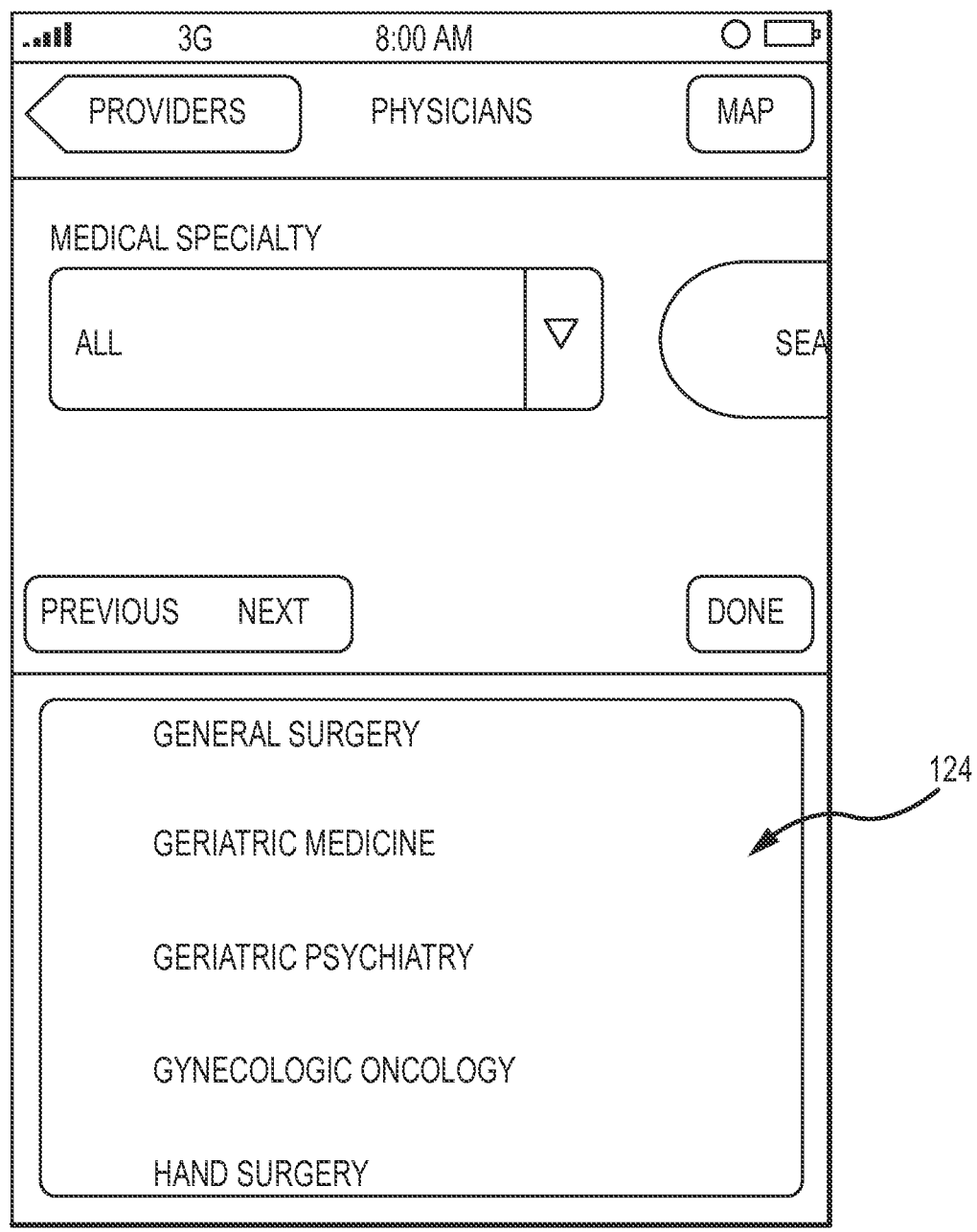

FIG. 28 shows a specialty selection screen 124. The specialty screen 124 may include provider list that may be accessed by way of either provider link 66 or a provider info screen 84. The specialty selection screen 124 may allow a user to filter the provider list 82 by the specialty of the provider. In this regard, the user may sort the providers that have been provided corresponding to the location of the provider or by the provider's specialty.

In this regard, the user may, after having researched a disease or symptom, determine the specialist most appropriate to provide treatment for the disease or symptom of interest. The user may then also use the user device 10 to determine nearby specialist capable of providing treatment. Further still, if the user has indicated a healthcare network to which they belong, the provider list may be further narrowed to show only providers within the user's healthcare network. If the user still desires information regarding the available specialists, the user device 10 may be used to access such information (e.g., cost information, user reviews of providers, administrative information regarding each provider, promotional information about providers, etc.).

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Moreover, while the invention has primarily been described in the context of obtaining actionable medical information, various aspects of the invention are applicable in other contexts. For example, the invention can be adapted to obtain legal information, information regarding vehicle repairs and in other contexts, for example, where there are barriers in matching the needs of a user to actionable information regarding the subject matter. Accordingly, it should be understood that only some embodiment and variants thereof have been shown and described and that all changes and modifications that come within the spirit of the invention are desired to be protected.

What is claimed is:

1. A method of providing medical information, the method comprising:
   receiving, at a computer-based processing system, information regarding a symptom from a user;
   correlating, by said system, said information regarding said symptom to at least one condition that presents said symptom;
   obtaining, at said system, healthcare network information regarding a healthcare network to which the user belongs;
   acquiring, at said system, information regarding a location of said user;
   identifying, by said system, a plurality of medical providers according to provider-type based on at least said condition, said healthcare network information, and said location of said user;

determining, by said system, an indication of appropriateness for each provider-type to treat said condition based on a condition severity level each medical provider is equipped to treat, wherein the indication is either positive to indicate that the provider-type is appropriate when the medical provider is equipped to treat said condition severity level, or negative to indicate that the provider-type is not appropriate when the medical provider is not equipped to treat said condition severity level;

presenting to said user, by said system, with a user interface of said system, a provider-type selection screen comprising a stratified list of provider-types designated with the determined indication of appropriateness;

receiving, by said system, a provider-type selection; and displaying, by said system, information regarding said plurality of medical providers that are associated with said selection.

2. The method of claim 1, wherein said acquiring comprises detecting, at said system, said location of said user.

3. The method of claim 2, wherein said detecting comprises utilizing a global positioning system (GPS) receiver to determine the location of said user.

4. The method of claim 1, further comprising:
providing to said user, using the system, a structured web search based on at least one of said symptom and said condition.

5. The method of claim 4, wherein said structured web search is directed to a description of said condition, symptoms of said condition, work-up of said condition, treatment of said condition, disease course of said condition, prognosis of said condition, new research on said condition, images of said condition, and videos of said condition.

6. The method of claim 1, wherein said condition severity level each medical provider is equipped to treat is based at least in part on information regarding facilities.

7. The method of claim 6, wherein information regarding facilities comprises at least one of hours of operation, staffing information, and real-time wait times.

8. The method of claim 1, wherein said information regarding said plurality of medical providers comprises location information regarding said plurality of medical providers in relation to said location of said user.

9. The method of claim 1, wherein said acquiring comprises receiving, at said system, information regarding a location of said user from said user.

10. The method of claim 1, wherein said identifying is based on at least said condition, said healthcare network information, and a medical specialty associated with the treatment of said condition.

11. The method of claim 1, wherein said obtaining comprises obtaining, at said system, said healthcare network information from the user.

12. The method of claim 1, wherein said obtaining comprises determining, using said system, said healthcare network information based on a network accessed by said user.

13. The method of claim 1, wherein said obtaining comprises inferring, using said system, said healthcare network information based on user information provided by said user.

14. The method of claim 1, wherein said information regarding said plurality of medical providers comprises at least one link to a website.

15. The method of claim 1, wherein said information regarding said plurality of medical providers comprises a cost estimate associated with a treatment of said condition.

16. The method of claim 1, wherein said information regarding said plurality of medical providers comprises information regarding a cost specialist to assist in determining proper costs regarding a treatment of said condition.

17. The method of claim 1, wherein said information regarding said plurality of medical providers comprises quality reports regarding said plurality of medical providers.

18. The method of claim 1, further comprising:
receiving from the user, at said system, feedback regarding a facility.

19. The method of claim 1, wherein said provider-types comprise at least emergency department, urgent care, retail clinic, physicians, and pharmacy.

20. The method of claim 1, wherein said positive indication to indicate that the provider is appropriate is a check-mark, and said negative indication to indicate that the provider is not appropriate is an x-mark.

21. A computer-based processing system for providing medical information, the system comprising:

a processor, in operative communication with at least one database containing condition information, configured to obtain healthcare network information regarding a healthcare network to which a user belongs;

said processor being configured to access said at least one database and correlate information regarding a symptom to at least one condition that presents said symptom;

input structure, executed by said processor and engageable by said user, configured to receive input from said user comprising information regarding said symptom;

a location determination module, in operative communication with said processor, configured to interpret location information regarding a user and utilize said location information to provide to said processor a user location;

said processor is configured to identify a plurality of medical providers according to provider-type based on said condition, said healthcare network information, and said user location;

said processor is configured to determine an indication of appropriateness for each provider-type to treat said condition based on a condition severity level each medical provider is equipped to treat, wherein the indication is either positive to indicate that the provider-type is appropriate when the medical provider is equipped to treat said condition severity level, or negative to indicate that the provider-type is not appropriate when the medical provider is not equipped to treat said condition severity level;

a user interface, controlled by said processor, configured to present a provider-type selection screen comprising a stratified list of provider-types designated with the determined indication of appropriateness;

said input structure is configured to receive a provider-type selection; and said user interface is configured to display information regarding said plurality of medical providers that are associated with said selection.

22. The system of claim 21, wherein said location determination module receives location information from a source remote from said system.

23. The system of claim 22, wherein said location information is obtained using a network based technique.

24. The system of claim 23, wherein said network based technique comprises at least one of a handset-based cell location method, cell sector method, microcell method, angle of arrival method, time difference of arrival method, and signal strength method.

25. The system of claim 21, wherein said condition severity level each medical provider is equipped to treat is based at least in part on information regarding facilities.

26. The system of claim 25, wherein information regarding facilities comprises at least one of hours of operation, staffing information, and real-time wait times.

27. The system of claim 21, wherein said information regarding said plurality of medical providers comprises location information regarding said plurality of medical providers in relation to said location of said user.

28. The system claim 21, wherein said location determination module comprises a global positioning system (GPS) receiver.

29. The system of claim 21, wherein said location determination module is in operative communication with said input structure and said location information is input by said user.

30. The system of claim 21, wherein said processor is operative to receive said healthcare network information from said user via said input structure.

31. The system of claim 21, wherein said processor is operative to receive said healthcare network information based on a network accessed by said user.

32. The system of claim 21, wherein said processor is operative to infer said healthcare network information based on user information provided by said user.

33. The system of claim 21, wherein the at least one database comprises at least one of a procedure database, a disease database, a symptoms database, and a provider's database.

34. The system of claim 21, wherein said processor is operative to identify said plurality of medical providers based on said condition, said healthcare network information, and a medical specialty associated with the treatment of said condition.

35. The system of claim 21, further comprising:
a connection to at least one of a data network and a telephone network,
wherein said user may operate said input structure to activate at least one of said data network and said telephone network based on said information regarding said plurality of medical providers.

36. The system of claim 21, wherein said provider-types comprise at least emergency department, urgent care, retail clinic, physicians, and pharmacy.

37. The system of claim 21, wherein said positive indication to indicate that the provider is appropriate is a checkmark, and said negative indication to indicate that the provider is not appropriate is an x-mark.

38. A user device for obtaining medical information, the user device comprising:
input structure, executed by a microprocessor at the user device, configured to receive healthcare network information regarding a healthcare network to which a user belongs and information regarding a symptom of said user;
said microprocessor being configured to correlate said information regarding said symptom of said user to at least one condition that presents said symptom;
a location determination module, executed by said microprocessor at the user device, and comprising a global positioning system (GPS) receiver, configured to interpret location information received at said GPS receiver and utilize said location information to provide to said microprocessor a user location free from location information input by the user;
a network interface, executed by said microprocessor, configured to transmit user information received by said input structure and said location determination module, respectively, including at least said healthcare network information, said user location, and said information condition to a network platform, and receive information identifying a plurality of medical providers according to provider-type from said network platform in response to said transmitting;
said microprocessor is configured to determine an indication of appropriateness for each provider-type to treat said condition based on a condition severity level each medical provider is equipped to treat, wherein the indication is either positive to indicate that the provider-type is appropriate when the medical provider is equipped to treat said condition severity level, or negative to indicate that the provider-type is not appropriate when the medical provider is not equipped to treat said condition severity level;
a user interface, executed by said microprocessor, configured to present a provider-type selection screen comprising a stratified list of provider-types designated with the determined indication of appropriateness;
said input structure is configured to receive a provider-type selection; and
said user interface is configured to display information regarding said plurality of medical providers that are associated with said selection.

39. The user device of claim 38, wherein said condition severity level each medical provider is equipped to treat is based at least in part on information regarding facilities.

40. The user device of claim 39, wherein information regarding facilities comprises at least one of hours of operation, staffing information, and real-time wait times.

41. The user device of claim 38, wherein said medical provider information comprises location information regarding a plurality of medical providers in relation to said location of said user.

42. The user device of claim 38, wherein said healthcare network information is received from said user.

43. The user device of claim 38, wherein said healthcare network information is based on a network accessed by said user.

44. The user device of claim 38, wherein said healthcare network information is based on user information provided by said user.

45. The user device of claim 38, wherein said network platform accesses at least one database comprising at least one of a procedure database, a disease database, a symptoms database, and a provider's database.

46. The user device of claim 38, wherein said medical provider information is based on said condition, said healthcare network information, and a medical specialty associated with the treatment of said condition.

47. The user device of claim 38, further comprising:
a connection to at least one of a data network and a telephone network,
wherein said user may operate said input structure to activate at least one of said data network and said telephone network based on said medical provider information.

48. The user device of claim 38, wherein said provider-types comprise at least emergency department, urgent care, retail clinic, physicians, and pharmacy.

49. The user device of claim 38, wherein said positive indication to indicate that the provider is appropriate is a check-mark, and said negative indication to indicate that the provider is not appropriate is an x-mark.

* * * * *